(12) United States Patent
Krulevitch et al.

(10) Patent No.: US 7,944,366 B2
(45) Date of Patent: May 17, 2011

(54) MALFUNCTION DETECTION WITH DERIVATIVE CALCULATION

(75) Inventors: Peter Krulevitch, Pleasanton, CA (US); Sebastian Bohm, Los Gatos, CA (US); Mingqi Zhao, San Jose, CA (US); Deon Anex, Livermore, CA (US)

(73) Assignee: Lifescan, Inc., Milpitas, CA (US)

( * ) Notice: Subject to any disclaimer, the term of this patent is extended or adjusted under 35 U.S.C. 154(b) by 1276 days.

(21) Appl. No.: 11/532,691

(22) Filed: Sep. 18, 2006

(65) Prior Publication Data

US 2007/0062250 A1    Mar. 22, 2007

Related U.S. Application Data

(60) Provisional application No. 60/718,572, filed on Sep. 19, 2005, provisional application No. 60/718,397, filed on Sep. 19, 2005, provisional application No. 60/718,412, filed on Sep. 19, 2005, provisional application No. 60/718,577, filed on Sep. 19, 2005, provisional application No. 60/718,578, filed on Sep. 19, 2005, provisional application No. 60/718,364, filed on Sep. 19, 2005, provisional application No. 60/718,399, filed on Sep. 19, 2005, provisional application No. 60/718,400, filed on Sep. 19, 2005, provisional application No. 60/718,398, filed on Sep. 19, 2005, provisional application No. 60/718,289, filed on Sep. 19, 2005.

(51) Int. Cl.
*G08B 21/00* (2006.01)
*A61M 31/00* (2006.01)
*A61M 37/00* (2006.01)
*A61M 1/00* (2006.01)
*G01F 25/00* (2006.01)
*B23H 11/00* (2006.01)
*G01R 31/00* (2006.01)

(52) U.S. Cl. .......... 340/679; 604/48; 604/131; 604/151; 73/1.16; 204/275.1; 324/500

(58) Field of Classification Search .................. 340/679; 73/1.16; 604/48, 131, 151; 324/500; 204/275.1
See application file for complete search history.

(56) References Cited

U.S. PATENT DOCUMENTS 3,623,474 A    11/1971    Heilman et al.
(Continued)

FOREIGN PATENT DOCUMENTS

WO    WO 03/071930    9/2003

OTHER PUBLICATIONS

International Search Report, from corresponding PCT/US06/36165, mailed Apr. 19, 2007.

(Continued)

*Primary Examiner* — George A Bugg
*Assistant Examiner* — Jack Wang

(57) ABSTRACT

Systems and methods of detecting occlusions and fluid-loss conditions (e.g., disconnects and/or leakages) in an infusion pump are discussed. For example, electrokinetic infusion pumps may develop an occlusion in the fluid flow path, which can disrupt control of fluid dispersed from the pump. As well, an infusion set disconnect can also result in a fluid-loss that can be disruptive. Such disruptions can be troublesome to systems that control the infusion pump, such as closed loop controllers. Accordingly, systems and methods described herein can be used to detect such occlusions and fluid-loss conditions during infusion pump operation. For example, a position sensor can be used to monitor fluid flow from the infusion pump, with the measurement being compared with an expected value to detect an occlusion or fluid-loss condition. Other algorithms for utilizing the position sensor are also described.

28 Claims, 19 Drawing Sheets

U.S. PATENT DOCUMENTS

| | | | |
|---|---|---|---|
| 3,701,345 A | 10/1972 | Heilman et al. | |
| 4,273,122 A | 6/1981 | Whitney et al. | |
| 4,320,757 A | 3/1982 | Whitney et al. | |
| 4,342,312 A | 8/1982 | Whitney et al. | |
| 4,364,385 A * | 12/1982 | Lossef | 424/424 |
| 4,529,401 A | 7/1985 | Leslie et al. | |
| 4,541,787 A | 9/1985 | DeLong | |
| 4,636,144 A | 1/1987 | Abe et al. | |
| 4,779,614 A | 10/1988 | Moise | |
| 4,833,384 A | 5/1989 | Munro et al. | |
| 4,838,857 A | 6/1989 | Strowe et al. | |
| 4,884,013 A | 11/1989 | Jackson et al. | |
| 4,921,480 A | 5/1990 | Sealfon | |
| 4,943,279 A | 7/1990 | Samiotes et al. | |
| 4,952,205 A | 8/1990 | Mauerer et al. | |
| 5,078,683 A | 1/1992 | Sancoff et al. | |
| 5,250,027 A | 10/1993 | Lewis et al. | |
| 5,378,231 A | 1/1995 | Johnson et al. | |
| 5,411,482 A | 5/1995 | Campbell | |
| 5,453,382 A | 9/1995 | Novotny et al. | |
| 5,478,211 A | 12/1995 | Dominiak et al. | |
| 5,482,438 A | 1/1996 | Anderson et al. | |
| 5,482,446 A | 1/1996 | Williamson et al. | |
| 5,531,697 A * | 7/1996 | Olsen et al. | 604/131 |
| 5,531,698 A * | 7/1996 | Olsen | 604/131 |
| 5,647,853 A | 7/1997 | Feldmann et al. | |
| 5,658,133 A | 8/1997 | Anderson et al. | |
| 5,882,338 A | 3/1999 | Gray | |
| 5,925,022 A * | 7/1999 | Battiato et al. | 604/208 |
| 5,982,401 A * | 11/1999 | Fassler et al. | 346/140.1 |
| 5,985,119 A | 11/1999 | Zanzucchi et al. | |
| 5,997,501 A | 12/1999 | Gross et al. | |
| 6,004,292 A * | 12/1999 | Battiato et al. | 604/123 |
| 6,013,057 A | 1/2000 | Danby et al. | |
| 6,013,164 A | 1/2000 | Paul et al. | |
| 6,019,745 A | 2/2000 | Gray | |
| 6,019,882 A | 2/2000 | Paul et al. | |
| 6,099,502 A * | 8/2000 | Duchon et al. | 604/131 |
| 6,120,665 A | 9/2000 | Chiang et al. | |
| 6,123,686 A * | 9/2000 | Olsen et al. | 604/151 |
| 6,129,517 A | 10/2000 | Danby et al. | |
| 6,129,668 A | 10/2000 | Haynor et al. | |
| 6,164,921 A | 12/2000 | Moubayed et al. | |
| 6,171,276 B1 | 1/2001 | Lippe et al. | |
| 6,195,887 B1 | 3/2001 | Danby et al. | |
| 6,211,670 B1 | 4/2001 | DeWilde et al. | |
| 6,213,723 B1 | 4/2001 | Danby et al. | |
| 6,263,230 B1 | 7/2001 | Haynor et al. | |
| 6,312,393 B1 | 11/2001 | Abreu | |
| 6,344,030 B1 * | 2/2002 | Duchon et al. | 604/131 |
| 6,362,591 B1 | 3/2002 | Moberg | |
| 6,485,461 B1 | 11/2002 | Mason et al. | |
| 6,485,465 B2 | 11/2002 | Moberg et al. | |
| 6,555,986 B2 | 4/2003 | Moberg | |
| 6,568,922 B1 | 5/2003 | Winsel | |
| 6,582,393 B2 | 6/2003 | Sage, Jr. | |
| 6,589,229 B1 | 7/2003 | Connelly et al. | |
| 6,607,509 B2 | 8/2003 | Bobroff et al. | |
| 6,656,148 B2 | 12/2003 | Das et al. | |
| 6,659,980 B2 | 12/2003 | Moberg et al. | |
| 6,669,909 B2 | 12/2003 | Shvets et al. | |
| 6,692,457 B2 | 2/2004 | Flaherty | |
| 6,719,535 B2 | 4/2004 | Rakestraw et al. | |
| 6,739,478 B2 | 5/2004 | Bach et al. | |
| 6,740,059 B2 | 5/2004 | Flaherty | |
| 6,742,992 B2 | 6/2004 | Davis | |
| 6,830,562 B2 | 12/2004 | Mogensen et al. | |
| 6,929,619 B2 | 8/2005 | Fago et al. | |
| 6,942,636 B2 | 9/2005 | Holst et al. | |
| 7,025,226 B2 * | 4/2006 | Ramey | 222/1 |
| 7,145,330 B2 | 12/2006 | Xiao | |
| 7,193,521 B2 | 3/2007 | Moberg et al. | |
| 7,588,046 B1 * | 9/2009 | Erickson | 137/1 |
| 2001/0034502 A1 * | 10/2001 | Moberg et al. | 604/154 |
| 2001/0039398 A1 * | 11/2001 | Fowler et al. | 604/151 |
| 2002/0052574 A1 * | 5/2002 | Hochman et al. | 604/31 |
| 2002/0076825 A1 * | 6/2002 | Cheng et al. | 436/174 |
| 2002/0151854 A1 * | 10/2002 | Duchon et al. | 604/197 |
| 2002/0177237 A1 * | 11/2002 | Shvets et al. | 436/180 |
| 2003/0018304 A1 | 1/2003 | Sage | |
| 2003/0040700 A1 * | 2/2003 | Hickle et al. | 604/67 |
| 2003/0069369 A1 | 4/2003 | Belenkaya et al. | |
| 2003/0073954 A1 | 4/2003 | Moberg et al. | |
| 2003/0078534 A1 * | 4/2003 | Hochman et al. | 604/67 |
| 2003/0167035 A1 * | 9/2003 | Flaherty et al. | 604/67 |
| 2003/0212379 A1 | 11/2003 | Bylund et al. | |
| 2003/0213297 A1 | 11/2003 | Sage et al. | |
| 2003/0233069 A1 | 12/2003 | Gillespie et al. | |
| 2003/0236489 A1 * | 12/2003 | Jacobson et al. | 604/67 |
| 2004/0013715 A1 | 1/2004 | Wnek et al. | |
| 2004/0019321 A1 | 1/2004 | Sage et al. | |
| 2004/0074768 A1 | 4/2004 | Anex et al. | |
| 2004/0074784 A1 | 4/2004 | Anex et al. | |
| 2004/0082908 A1 * | 4/2004 | Whitehurst et al. | 604/67 |
| 2004/0085215 A1 | 5/2004 | Moberg et al. | |
| 2004/0133166 A1 * | 7/2004 | Moberg et al. | 604/151 |
| 2004/0207396 A1 * | 10/2004 | Xiao | 324/244 |
| 2005/0051580 A1 | 3/2005 | Ramey | |
| 2005/0143864 A1 | 6/2005 | Blomquist | |
| 2005/0192494 A1 | 9/2005 | Ginsberg | |
| 2005/0214129 A1 | 9/2005 | Greene et al. | |
| 2005/0247558 A1 | 11/2005 | Anex et al. | |
| 2006/0047538 A1 | 3/2006 | Condurso et al. | 705/3 |
| 2007/0048153 A1 * | 3/2007 | Yeh | 417/412 |
| 2007/0062251 A1 * | 3/2007 | Anex | 73/1.36 |
| 2007/0066939 A1 * | 3/2007 | Krulevitch et al. | 604/152 |
| 2007/0066940 A1 * | 3/2007 | Karunaratne et al. | 604/152 |
| 2007/0093752 A1 * | 4/2007 | Zhao et al. | 604/131 |
| 2007/0093753 A1 * | 4/2007 | Krulevitch et al. | 604/131 |

OTHER PUBLICATIONS

Owner's Manual, Alza E-Trans Transdermal Delivery, Alza Corporation, Mountain View, California, Jun. 17-18, 2003 (4 pgs).

Owner's Manual, Temposonics LK Embeddable Sensors, OEM Integrator's Manual, MTS Systems Corporation, Cary, NC 27513, 550562 Rev. B, Mar. 1998 (11 pgs).

Bratland, T. et al., "Linear Position Sensing Using Magnetoresistive Sensors," Honeywell Solid State Electronics Center (Apr. 8, 2005), entire document at http://web/20050408082814/http:// www.ssec.Honeywell.com/magnetic/datasheets/linearpositionsensing.pdf.

International Search Report, from PCT/US06/36340, mailed Aug. 1, 2007.

International Search Report, from PCT/US06/36330, mailed Sep. 12, 2007.

International Search Report, from PCT/US06/36326, mailed Sep. 13, 2007.

International Search Report, from PCT/US06/36173, mailed Sep. 17, 2007.

* cited by examiner

MALFUNCTION DETECTION WITH
DERIVATIVE CALCULATION

CROSS-REFERENCE TO RELATED
APPLICATIONS

The present application claims the benefit of the following U.S. Provisional Applications, all filed on Sep. 19, 2005: Ser. No. 60/718,572, and entitled "Electrokinetic Infusion Pump with Detachable Controller and Method of Use"; Ser. No. 60/718,397, and entitled "A Method of Detecting Occlusions in an Electrokinetic Pump Using a Position Sensor"; Ser. No. 60/718,412, and entitled "A Magnetic Sensor Capable of Measuring a Position at an Increased Resolution"; Ser. No. 60/718,577, and entitled "A Drug Delivery Device Using a Magnetic Position Sensor for Controlling a Dispense Rate or Volume"; Ser. No. 60/718,578, and entitled "Syringe-Type Electrokinetic Infusion Pump and Method of Use"; Ser. No. 60/718,364, and entitled "Syringe-Type Electrokinetic Infusion Pump for Delivery of Therapeutic Agents"; Ser. No. 60/718,399, and entitled "Electrokinetic Syringe Pump with Manual Prime Capability and Method of Use"; Ser. No. 60/718,400, and entitled "Electrokinetic Pump Integrated within a Plunger of a Syringe Assembly"; Ser. No. 60/718, 398, and entitled "Reduced Size Electrokinetic Pump Using an Indirect Pumping Mechanism with Hydraulic Assembly"; and Ser. No. 60/718,289, and entitled "Manual Prime Capability of an Electrokinetic Syringe Pump and Method of Use." The present application is also related to the following applications, all filed currently herewith: "Infusion Pump with Closed Loop Control and Algorithm", "Malfunction Detection via Pressure Pulsation" "Infusion Pumps with a Position Sensor" "Systems and Methods for Detecting a Partition Position in an Infusion Pump", "Electrokinetic Infusion Pump System". All of the applications recited in this paragraph are hereby incorporated by reference herein in their entirety.

FIELD OF THE INVENTION

The present invention relates, in general, to medical devices and systems and, in particular, to infusion pumps, infusion pump systems and associated methods.

BACKGROUND OF THE INVENTION

Electrokinetic pumps provide for liquid displacement by applying an electric potential across a porous dielectric media that is filled with an ion-containing electrokinetic solution. Properties of the porous dielectric media and ion-containing solution (e.g., permittivity of the ion-containing solution and zeta potential of the solid-liquid interface between the porous dielectric media and the ion-containing solution) are predetermined such that an electrical double-layer is formed at the solid-liquid interface. Thereafter, ions of the electrokinetic solution within the electrical double-layer migrate in response to the electric potential, transporting the bulk electrokinetic solution with them via viscous interaction. The resulting electrokinetic flow (also known as electroosmotic flow) of the bulk electrokinetic solution is employed to displace (i.e., "pump") a liquid. Further details regarding electrokinetic pumps, including materials, designs, and methods of manufacturing are included in U.S. patent application Ser. No. 10/322,083 filed on Dec. 17, 2002, which is hereby incorporated in full by reference.

SUMMARY OF THE INVENTION

One exemplary embodiment is directed to a method of detecting a malfunction in an infusion pump using a derivative calculation. Generally, the malfunction detection method can include performing one or more activation/de-activation cycles with an infusion pump while determining a position of a non-mechanically driven movable partition disposed in the pump using, for example, a magnetic position sensor, calculating a derivative for each of the cycles, calculating a moving average using the calculated derivative values, and comparing the calculated moving average with a pre-determined threshold value to determine whether the infusion pump is malfunctioning. The steps need not occur in the order presented. For example, in one exemplary embodiment, determining a position of the movable partition can occur before de-activating the infusion pump. In one embodiment, the infusion pump can be an electrokinetic infusion pump. The derivative can be based on a change in position of the movable partition with respect to a change in the number of fluid shots released by the infusion pump. In one embodiment, calculating the derivative can include using the last two known positions of the movable partition for each of the cycles. Calculating the moving average can include multiplying the calculated derivative value by a weighting factor. The pre-determined threshold value can represent a variety of infusion pump operating parameters.

In one embodiment, the pre-determined threshold value can be a minimum acceptable value for the calculated moving average. In this embodiment, comparing the calculated moving average to the pre-determined threshold value can further include triggering a positive occlusion flag if the calculated moving average is less than the pre-determined threshold value. The method can also include repeating the above steps and indicating the presence of an occlusion if the positive occlusion flag occurs at least a predetermined number of consecutive times. In an exemplary embodiment, indicating the presence of an occlusion can include generating an alarm signal.

In another embodiment, the pre-determined threshold value can be a maximum acceptable value for the calculated moving average. In this embodiment, comparing the calculated moving average to the pre-determined threshold value can further include triggering a positive fluid-loss flag if the calculated moving average is greater than the pre-determined threshold value. The method can also include repeating the above steps and indicating the presence of a fluid-loss condition if the positive fluid-loss flag occurs at least a predetermined number of consecutive times. In an exemplary embodiment, indicating the presence of a fluid-loss condition can include generating an alarm signal.

A system for detecting a malfunction in an infusion pump using a derivative calculation is also provided. The system can include an infusion pump having a non-mechanically driven movable partition disposed therein, a position sensor disposed on the pump, a controller associated with the pump, and a processor associated with the position sensor. In an exemplary embodiment, the infusion pump can be an electrokinetic infusion pump. A variety of configurations are available for the position sensor. For example, the position sensor can be a magnetic sensor, an optical sensor, or a linear variable differential transformer. The controller can be adapted to operate the infusion pump in an activate/de-activate cycle. The cycle can include activating the pump for a first pre-determined amount of time to induce movement of the movable partition and release a shot of fluid, and de-activating the pump for a second pre-determined amount of time. The processor can be adapted to determine whether the infusion pump is malfunctioning at least by comparing a calculated moving average of a plurality of derivatives to a pre-determined threshold value. Each derivative can be based on a change in position of the movable partition with respect to a change in the number of shots released by the pump. The processor can be configured to calculate the moving average based upon calculated derivatives from a selected number of cycles, for example from a last three or five cycles. As with the embodiments described above, the pre-determined threshold value can represent a variety of infusion pump operating parameters.

In one embodiment, the predetermined threshold value can be a minimum acceptable value for the calculated moving average. In this embodiment, the processor can be configured to provide a positive occlusion flag if the calculated moving average is less than the pre-determined threshold value. The processor can also be configured to produce an occlusion detection signal if the positive occlusion flag signal is produced after each of at least a predetermined number of consecutive cycles. In an exemplary embodiment, the predetermined number of cycles can be at least three.

In another embodiment, the pre-determined threshold value can be a maximum acceptable value for the calculated moving average. In this embodiment, the processor can be configured to provide a positive fluid-loss flag if the calculated moving average is greater than the pre-determined threshold value. The processor can also be configured to produce fluid-loss detection signal if the positive fluid-loss flag signal is produced after each of at least a predetermined number of consecutive cycles.

The malfunction detection system can further include an alarm coupled to the processor for producing an alarm signal when the processor determines that the infusion pump is malfunctioning.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
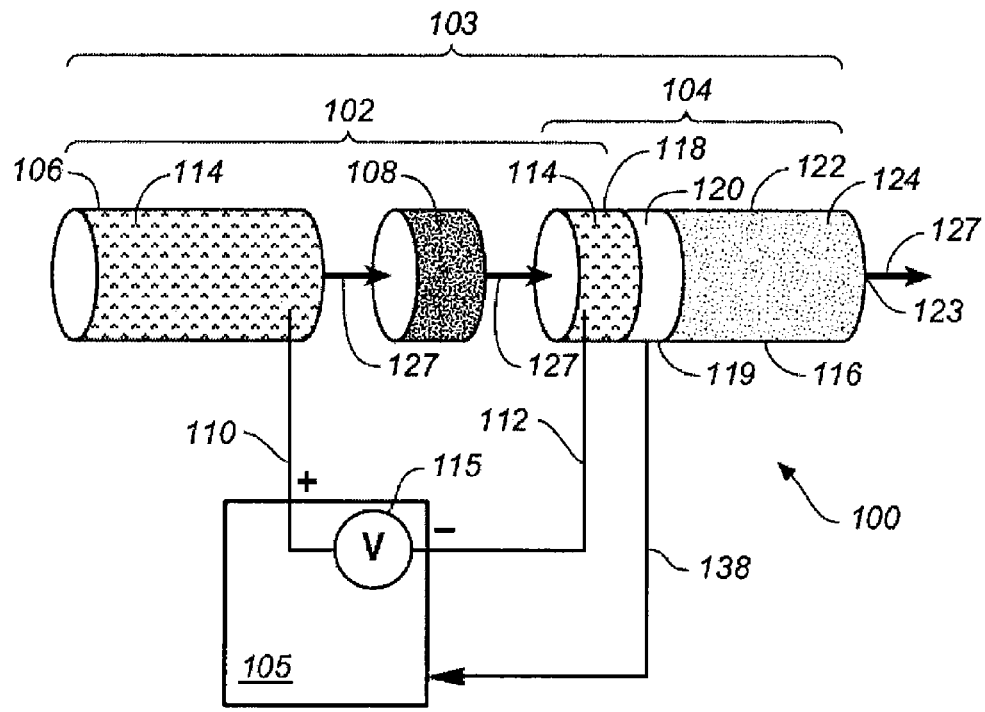
FIG. 1A is a schematic illustration of an electrokinetic pump in a first dispense position consistent with an embodiment of the invention, the pump including an electrokinetic engine, an infusion module, and a closed loop controller.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Embodiments of the present invention generally provide methods and systems for detecting malfunctions in infusion pumps. A variety of malfunctions are associated with the operation of infusion pumps. For example, occlusions, bubbles or other obstructions that form in an infusion set, can interfere with the flow from an infusion pump and result in inaccurate doses of infusion fluid. Other potential issues with infusion pumps include disconnects within the infusion set and leaks. The malfunction detection methods disclosed herein can include determining a first position of a movable partition of an infusion pump, activating the infusion pump to induce movement of the movable partition, de-activating the infusion pump, determining a second position of the movable partition, calculating a measured displacement based on the first and second positions of the movable partition, and comparing the measured displacement to pre-determined threshold value to determine whether the infusion pump is malfunctioning. The methods for detecting malfunctions in infusion pumps provided herein can work in conjunction with a variety of infusion pumps including, but not limited to, electrokinetic infusion pumps with closed loop control. Select embodiments of exemplary electrokinetic infusion pump systems are described below. Further details regarding infusion pumps with closed loop control suitable for use with the malfunction detection methods of the present invention are included co-pending applications entitled "Infusion Pump with Closed Loop Control and Algorithm" and "Electrokinetic Infusion Pump System", filed concurrently herewith and hereby incorporated by reference in their entirety.

Electrokinetic Infusion Pumps

Electrokinetic pumping can provide the driving force for displacing infusion liquid. Electrokinetic pumping (also known as electroosmotic flow) works by applying an electric potential across an electrokinetic porous media that is filled with electrokinetic solution. Ions in the electrokinetic solution form double layers in the pores of the electrokinetic porous media, countering charges on the surface of the electrokinetic porous media. Ions migrate in response to the electric potential, dragging the bulk electrokinetic solution with them. Electrokinetic pumping can be direct or indirect, depending upon the design. In direct pumping, infusion liquid is in direct contact with the electrokinetic porous media, and is in direct electrical contact with the electrical potential. In indirect pumping, infusion liquid is separated from the electrokinetic porous media and the electrokinetic solution by way of a moveable partition. Further details regarding electrokinetic pumps, including materials, designs, and methods of manufacturing, suitable for use in devices according to the present invention are included in U.S. patent application Ser. No. 10/322,083 filed on Dec. 17, 2002, and Ser. No. 11/112,867 filed on Apr. 21, 2005, which are hereby incorporated by reference in their entirety.

A variety of infusion liquids can be delivered with electrokinetic infusion pumps using closed loop control, including insulin for diabetes; morphine and/or other analgesics for pain; barbiturates and ketamine for anesthesia; anti-infective and antiviral therapies for AIDS; antibiotic therapies for preventing infection; bone marrow for immunodeficiency disorders, blood-borne malignancies, and solid tumors; chemotherapy for cancer; and dobutamine for congestive heart failure. The electrokinetic infusion pumps with closed loop control can also be used to deliver biopharmaceuticals. Biopharmaceuticals are difficult to administer orally due to poor stability in the gastrointestinal system and poor absorption. Biopharmaceuticals that can be delivered include monoclonal antibodies and vaccines for cancer, BNP-32 (Natrecor) for congestive heart failure, and VEGF-121 for preeclampsia. The electrokinetic infusion pumps with closed loop control can deliver infusion liquids to the patient in a number of ways, including subcutaneously, intravenously, or intraspinally. For example, the electrokinetic infusion pumps can deliver insulin subcutaneously as a treatment for diabetes, or can deliver stem cells and/or sirolimus to the adventitial layer in the heart via a catheter as a treatment for cardiovascular disease.

Figure 1B:
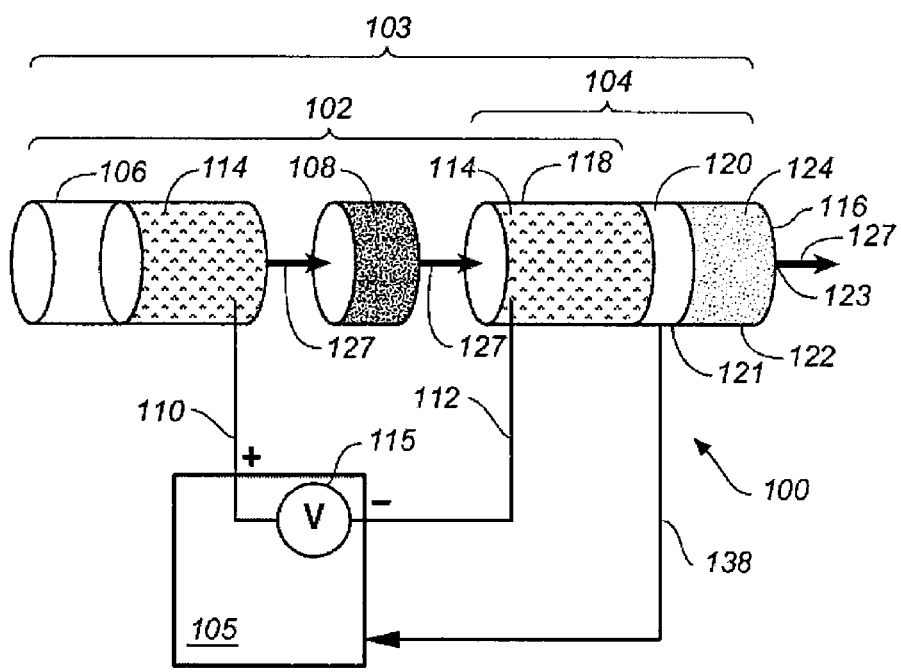
FIG. 1B is a schematic illustration of the electrokinetic pump of FIG. 1A in a second dispense position.

FIGS. 1A and 1B are schematic illustrations of an electrokinetic infusion pump with closed loop control 100 in accord with an exemplary embodiment. The electrokinetic infusion pump system illustrated in FIGS. 1A and 1B includes an electrokinetic infusion pump 103, and a closed loop controller 105. The electrokinetic infusion pump illustrated in FIG. 1A is in a first dispense position, while the pump illustrated in FIG. 1B is in a second dispense position. Electrokinetic infusion pump 103 includes electrokinetic engine 102 and infusion module 104. Electrokinetic engine 102 includes electrokinetic supply reservoir 106, electrokinetic porous media 108, electrokinetic solution receiving chamber 118, first electrode 110, second electrode 112, and electrokinetic solution 114. Closed loop controller 105 includes voltage source 115, and controls electrokinetic engine 102. Infusion module 104 includes infusion housing 116, electrokinetic solution receiving chamber 118, movable partition 120, infusion reservoir 122, infusion reservoir outlet 123, and infusion liquid 124. In operation, electrokinetic engine 102 provides the driving force for displacing infusion liquid 124 from infusion module 104. During fabrication, electrokinetic supply reservoir 106, electrokinetic porous media 108, and electrokinetic solution receiving chamber 118 are filled with electrokinetic solution 114. Before use, the majority of electrokinetic solution 114 is in electrokinetic supply reservoir 106, with a small amount in electrokinetic porous media 108 and electrokinetic solution receiving chamber 118. To displace infusion liquid 124, a voltage is established across electrokinetic porous media 108 by applying potential across first electrode 110 and second electrode 112. This causes electrokinetic pumping of electrokinetic solution 114 from electrokinetic supply reservoir 106, through electrokinetic porous media 108, and into electrokinetic solution receiving chamber 118. As electrokinetic solution receiving chamber 118 receives electrokinetic solution 114, pressure in electrokinetic solution receiving chamber 118 increases, forcing moveable partition 120 in the direction of arrows 127, i.e., the partition 120 is non-mechanically-driven. As moveable partition 120 moves in the direction of arrows 127, it forces infusion liquid 124 out of infusion reservoir outlet 123. Electrokinetic engine 102 continues to pump electrokinetic solution 114 until moveable partition 120 reaches the end nearest infusion reservoir outlet 123, displacing nearly all infusion liquid 124 from infusion reservoir 122.

Once again referring to the electrokinetic infusion pump with closed loop control 100 illustrated in FIGS. 1A and 1B, the rate of displacement of infusion liquid 124 from infusion reservoir 122 is directly proportional to the rate at which electrokinetic solution 114 is pumped from electrokinetic supply reservoir 106 to electrokinetic solution receiving chamber 118. The rate at which electrokinetic solution 114 is pumped from electrokinetic supply reservoir 106 to electrokinetic solution receiving chamber 118 is a function of the voltage and current applied across first electrode 110 and second electrode 112. It is also a function of the physical properties of electrokinetic porous media 108 and the physical properties of electrokinetic solution 114. As mentioned previously, further details regarding electrokinetic pumps, including materials, designs, and methods of manufacturing, suitable for use in devices according to the present invention are included in U.S. patent application Ser. No. 10/322,083 filed on Dec. 17, 2002, which has been incorporated by reference in its entirety.

In FIG. 1A, movable partition 120 is in first position 119, while in FIG. 1B, movable partition 120 is in second position 121. The position of movable partition 120 can be determined, and used by closed loop controller 105 to control the voltage and current applied across first electrode 110 and second electrode 112. By controlling the voltage and current applied across first electrode 110 and second electrode 112, the rate at which electrokinetic solution 114 is pumped from electrokinetic supply reservoir 106 to electrokinetic solution receiving chamber 118 and the rate at which infusion liquid 124 is pumped through infusion reservoir outlet 123 can be controlled. A closed loop controller can use the position of movable partition 120 to control the voltage and current applied to first electrode 110 and second electrode 112, and accordingly control infusion fluid delivered from the electrokinetic infusion pump.

Figure 4:
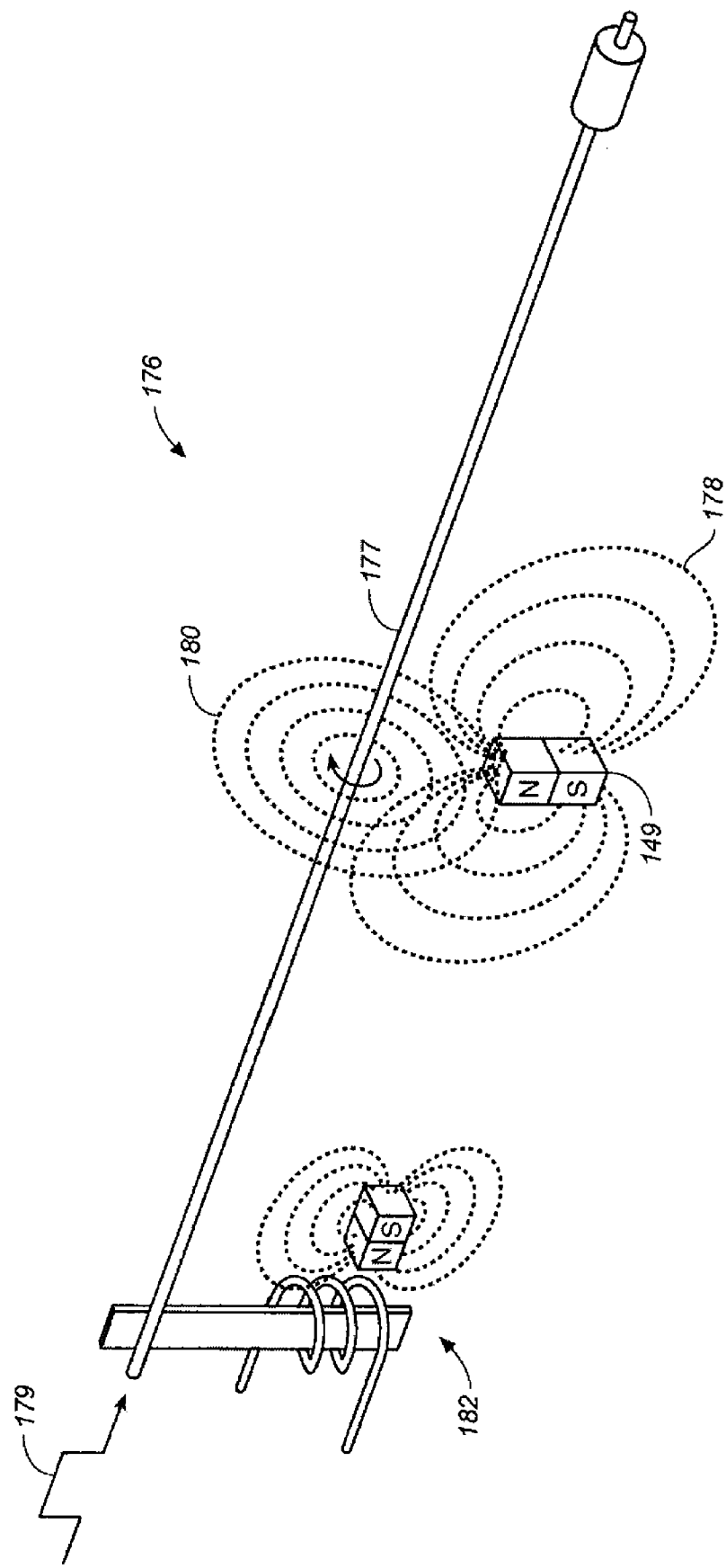
FIG. 4 is an illustration of a magnetic linear position detector as can be used in an electrokinetic infusion pump with closed loop control according to an embodiment of the present invention.

The position of movable partition 120 can be determined using a variety of techniques. In some embodiments, movable partition 120 can include a magnet, and a magnetic sensor can be used to determine its position. FIG. 4 illustrates the principles of one particular magnetic position sensor 176. Magnetic position sensor 176, suitable for use in this invention, can be purchased from MTS Systems Corporation, Sensors Division, of Cary, N.C. In magnetic position sensor 176, a sonic strain pulse is induced in magnetostrictive waveguide 177 by the momentary interaction of two magnetic fields. First magnetic field 178 is generated by movable permanent magnet 149 as it passes along the outside of magnetostrictive waveguide 177. Second magnetic field 180 is generated by current pulse 179 as it travels down magnetostrictive waveguide 177. The interaction of first magnetic field 178 and second magnetic field 180 creates a strain pulse. The strain pulse travels, at sonic speed, along magnetostrictive waveguide 177 until the strain pulse is detected by strain pulse detector 182. The position of movable permanent magnet 149 is determined by measuring the elapsed time between application of current pulse 179 and detection of the strain pulse at strain pulse detector 182. The elapsed time between application of current pulse 179 and arrival of the resulting strain pulse at strain pulse detector 182 can be correlated to the position of movable permanent magnet 149.

Other types of position detectors that include a magnetic sensor for identifying the position of a moveable partition that use a magnetic sensor can also be used such as Hall-Effect sensors. In a particular example, anisotropic magnetic resistive sensors can be advantageously used with infusion pumps, as described in the co-pending application entitled "Infusion Pumps with a Position Sensor", filed concurrently herewith and hereby incorporated herein by reference in its entirety. In other embodiments, optical components can be used to determine the position of a movable partition. Light emitters and photodetectors can be placed adjacent to an infusion housing, and the position of the movable partition determined by measuring variations in detected light. In still other embodiments, a linear variable differential transformer (LVDT) can be used. In embodiments where an LVDT is used, the moveable partition includes an armature made of magnetic material. A LVDT that is suitable for use in the present application can be purchased from RDP Electrosense Inc., of Pottstown, Pennsylvania. Those skilled in the art will appreciate that other types of position detectors can also be utilized, consistent with embodiments of the present invention.

Figure 3:
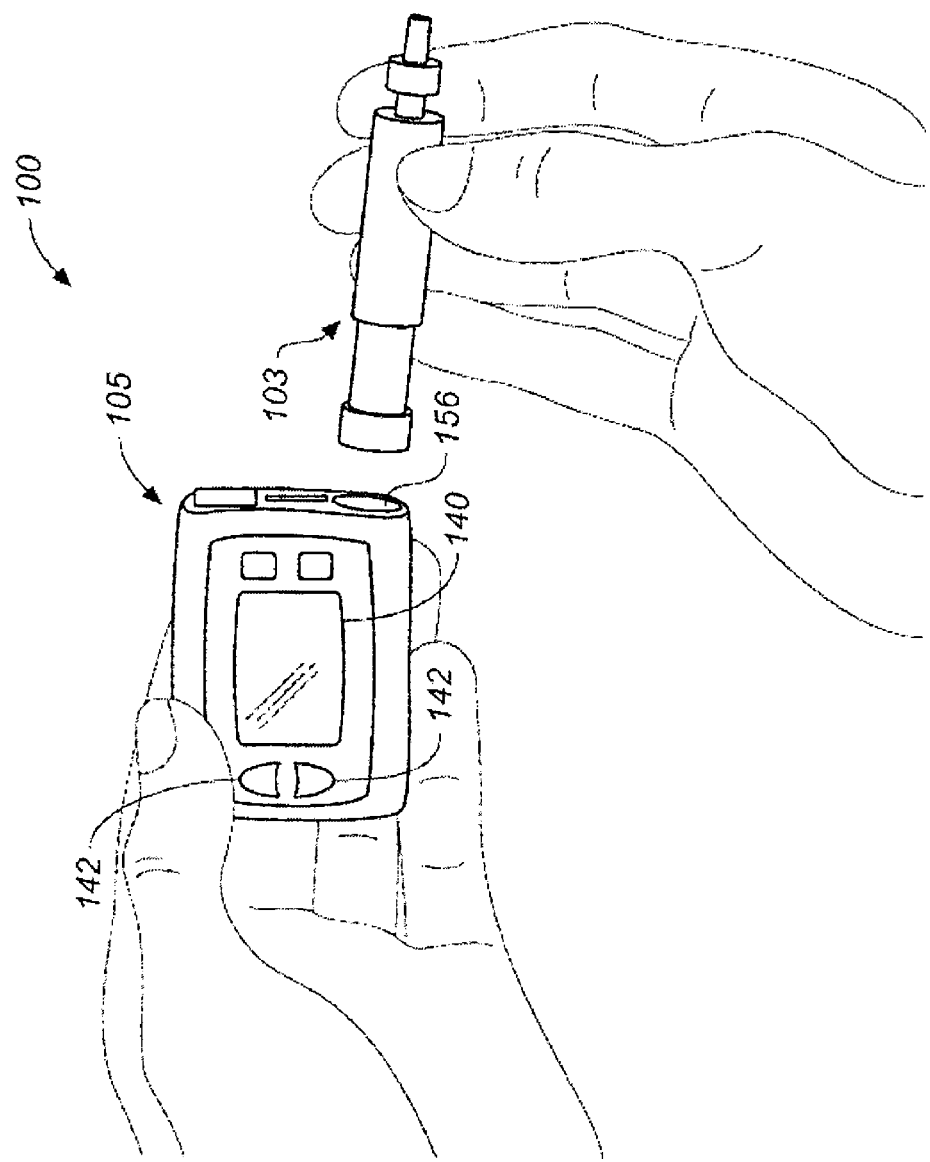
FIG. 3 is an illustration of an electrokinetic infusion pump with closed loop control according to an additional embodiment of the present invention.
Figure 5A:
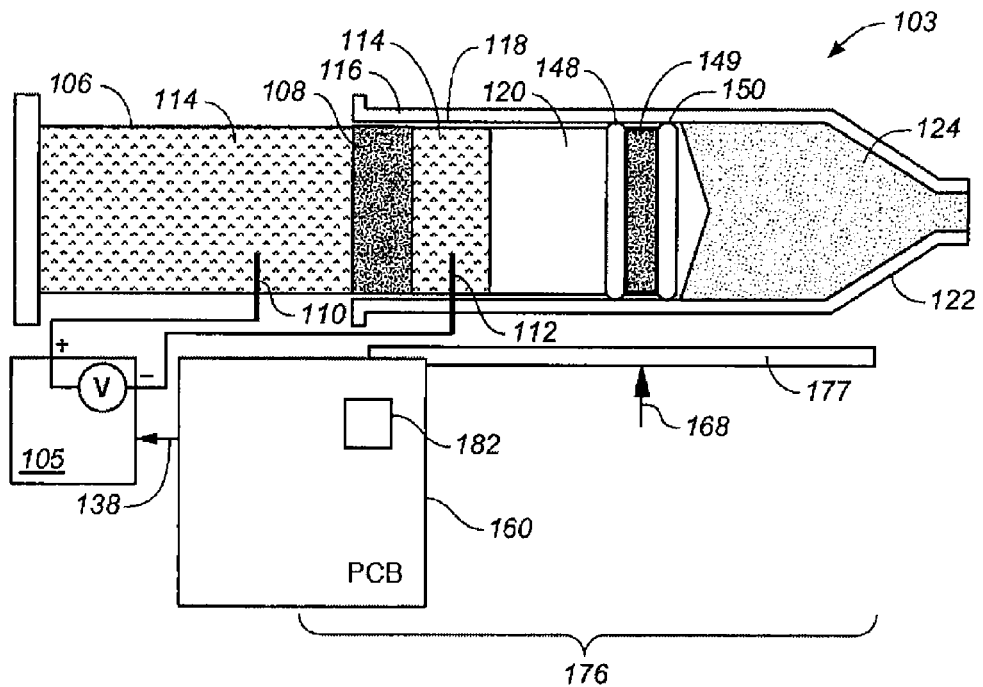
FIGS. 5A and 5B illustrate portions of an electrokinetic infusion pump with closed loop control according to an embodiment of the present invention, including an electrokinetic engine, an infusion module, a magnetostrictive waveguide, and a position sensor control circuit. The electrokinetic infusion pump with closed loop control illustrated in FIG. 5A is in a first dispense position, while the electrokinetic infusion pump with closed loop control illustrated in FIG. 5B is in a second dispense position.
Figure 5B:
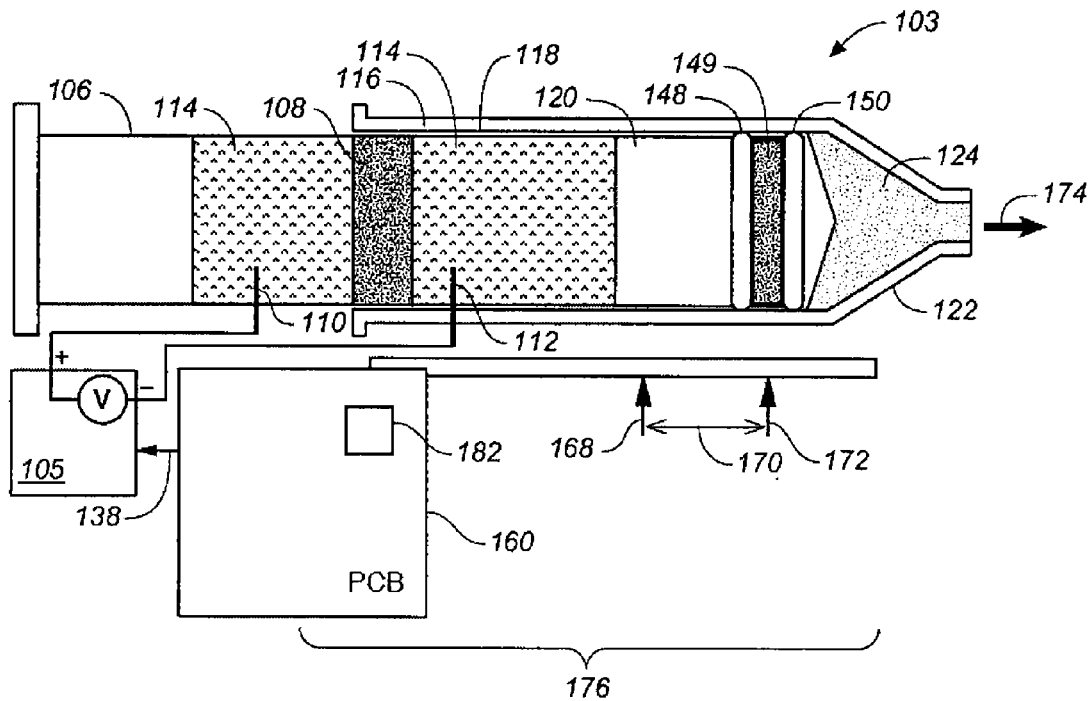
Figure 6:
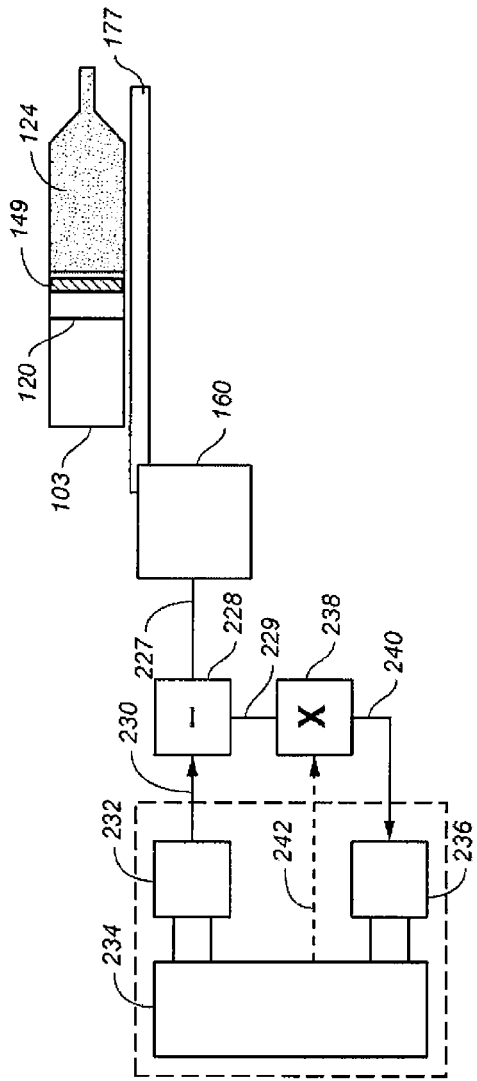
FIG. 6 is a block diagram of a sensor signal processing circuit that can be used in an electrokinetic infusion pump with closed loop control according to an additional embodiment of the present invention. The block diagram illustrated in FIG. 6 includes a microprocessor, a digital to analog converter, an analog to digital converter, a voltage nulling device, a voltage amplifier, a position sensor control circuit, a magnetostrictive waveguide, and an electrokinetic infusion pump.
Figure 8:
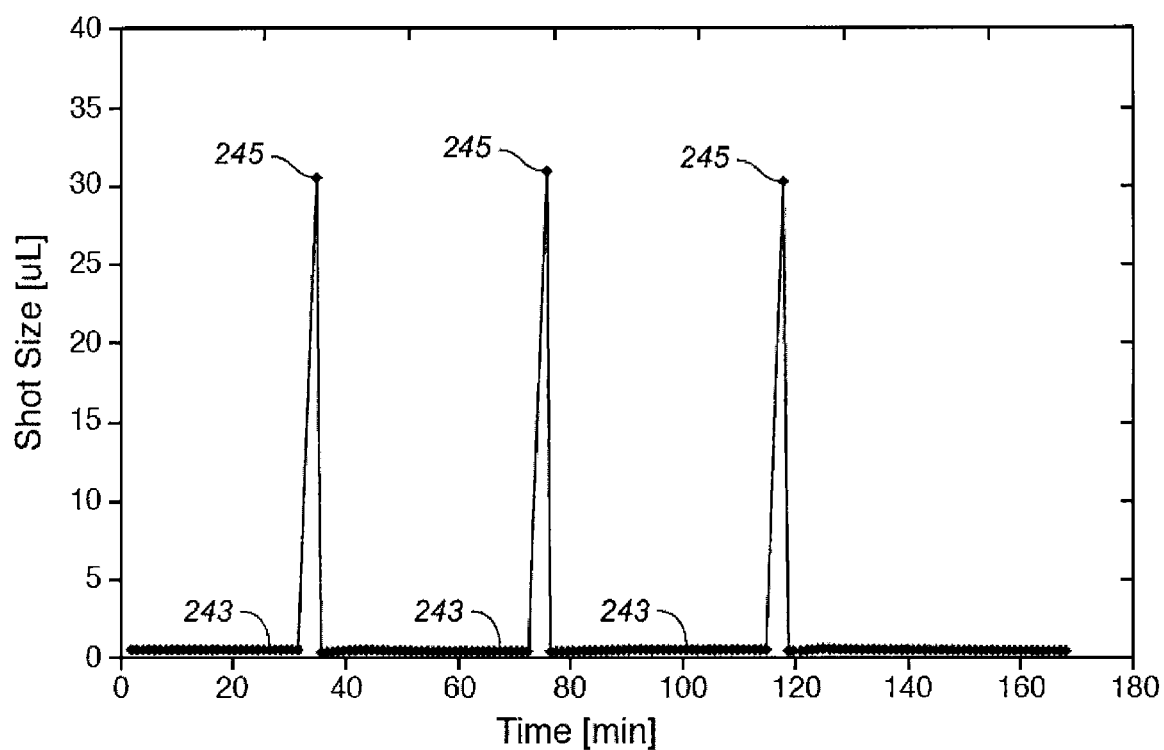
FIG. 8 is a graph showing the performance of the electrokinetic infusion pump with closed loop control illustrated in FIG. 7 in both basal and bolus modes.

Depending upon desired end use, electrokinetic engine 102 and infusion module 104 can be integrated into a single assembly, or can be separate and connected by tubing. Electrokinetic engine 102 and infusion module 104 illustrated in FIGS. 3, 5A, and 5B are integrated, while electrokinetic engine 102 and infusion module 104 illustrated in FIG. 8 are not integrated. Regardless of whether electrokinetic engine 102 and infusion module 104 are integrated, the position of movable partition 120 can be measured, and used to control the voltage and current applied across electrokinetic porous media 108. In this way, electrokinetic solution 114 and infusion liquid 124 can be delivered consistently in either an integrated or separate configuration.

Electrokinetic supply reservoir 106, as used in the electrokinetic infusion pump with closed loop control illustrated in FIGS. 1A, 1B, 3, 5A, 5B, 7 and 8, can be collapsible, at least in part. This allows the size of electrokinetic supply reservoir 106 to decrease as electrokinetic solution 114 is removed. Electrokinetic supply reservoir 106 can be constructed using a collapsible sack, or can include a moveable piston with seals. Also, infusion housing 116, as used in electrokinetic infusion pump with closed loop control in FIGS. 1A, 1B, 3, 5A, 5B, 7, and 8, is preferably rigid, at least in part. This makes it easier to displace moveable partition 120 than to expand infusion housing 116 as electrokinetic solution receiving chamber 118 receives electrokinetic solution 114 pumped from electrokinetic supply reservoir 106, and can provide more precise delivery of infusion liquid 124. Moveable partition 120 can be designed to prevent migration of electrokinetic solution 114 into infusion liquid 124, while decreasing resistance to displacement as electrokinetic solution receiving chamber 118 receives electrokinetic solution 114 pumped from electrokinetic supply reservoir 106. In some embodiments, moveable partition 120 includes elastomeric seals that provide intimate yet movable contact between moveable partition 120 and infusion housing 116. In some embodiments, moveable partition 120 is piston-like, while in other embodiments moveable partition 120 is fabricated using membranes and/or bellows. As mentioned previously, closed loop control can help maintain consistent delivery of electrokinetic solution 114 and infusion liquid 124, in spite of variations in resistance caused by variations in the volume of electrokinetic supply reservoir 106, by variations in the diameter of infusion housing 116, and/or by variations in back pressure at the user's infusion site.

Closed Loop Control Schemes

Various exemplary embodiments are directed to methods and systems for controlling the delivery of infusion liquids from an electrokinetic infusion pump. In particular embodiments, a closed loop control scheme can be utilized to control delivery of the infusion liquid. Although many of the various closed loop control schemes described in the present application are described in the context of their use with electrokinetic engines, embodiments using other engines are also within the scope of embodiments of the present invention. Closed loop control, as described in the present application, can be useful in many types of infusion pumps. These include pumps that use engines or driving mechanisms that generate pressure pulses in a hydraulic medium in contact with the movable partition in order to induce partition movement. These driving mechanisms can be based on gas generation, thermal expansion/contraction, and expanding gels and polymers, used alone or in combination with electrokinetic engines. As well, engines in infusion pumps that utilize a moveable partition to drive delivery an infusion fluid (e.g., non-mechanically driven partitions of an infusion pump such as hydraulically actuated positions) can include the closed loop control schemes described herein. Further details regarding electrokinetic infusion pumps with closed loop control suitable for use with the malfunction detection methods of the present invention are included in co-pending application entitled "Infusion Pump with Closed Loop Control and Algorithm" filed concurrently herewith and hereby incorporated by reference in its entirety.

Use of a closed loop control scheme with an electrokinetic infusion pump can compensate for variations that may cause inconsistent dispensing of infusion liquid. For example, with respect to FIGS. 1A and 1B, if flow of electrokinetic solution 114 varies as a function of the temperature of electrokinetic porous media 108, variations in the flow of infusion liquid 124 can occur if a constant voltage is applied across first electrode 110 and second electrode 112. By using closed loop control, the voltage across first electrode 110 and second electrode 112 can be varied based upon the position of movable partition 120 and the desired flow of infusion liquid 124. Another example of using closed loop control involves compensating for variations in flow caused by variations in down stream resistance to flow. In cases where there is minimal resistance to flow, lower voltages and current may be used to achieve a desired flow of electrokinetic solution 114 and infusion liquid 124. In cases where there is higher resistance to flow, higher voltages and current may be used to achieve a desired flow of electrokinetic solution 114 and infusion liquid 124. Since resistance to flow is often unknown and/or changing, variations in flow of electrokinetic solution 114 and infusion liquid 124 may result. By determining the position of movable partition 120, the current and voltage can be adjusted to deliver a desired flow rate of electrokinetic solution 114 and infusion liquid 124, even if the resistance to flow is changing. Another example of using closed loop control involves compensating for variation in flow caused by variation in the force required to push movable partition 120. Variations in friction between movable partition 120 and the inside surface of infusion housing 116 may cause variations in the force required to push movable partition 120. If a constant voltage and current are applied across electrokinetic porous media 108, variation in flow of electrokinetic solution 114 and infusion liquid 124 may result. By monitoring the position of movable partition 120, and varying the voltage and current applied across electrokinetic porous media 108, a desired flow rate of electrokinetic solution 114 and infusion liquid 124 can be achieved. Accordingly, in some embodiments, a closed loop control algorithm can utilize a correction factor, as discussed herein, to alter operation of a pump (e.g., using the correction factor to change the current and/or voltage applied across the electrokinetic pump's electrodes).

Electrokinetic infusion pumps that utilize a closed loop control scheme can operate in a variety of manners. For example, the pump can be configured to deliver a fluid shot amount in a continuous manner (e.g., maintaining a constant flow rate) by maintaining one or more pump operational parameters at a constant value. Non-limiting examples include flow rate of infusion fluid or electrokinetic solution, pressure, voltage or current across electrodes, and power output from a power source. In such instances, a closed loop control scheme can be used to control the operational parameter at or near the desired value.

In some embodiments, the pump is configured to deliver an infusion fluid by delivering a plurality of fluid shot amounts. For example, the electrokinetic infusion pump can be configured to be activated to deliver a shot amount of fluid. The amount can be determined using a variety of criteria such as a selected quantity of fluid or application of a selected voltage and/or current across the electrodes of the pump for a selected period of time. Following activation, the pump can be deactivated for a selected period of time, or until some operating parameter reaches a selected value (e.g., pressure in a chamber of the electrokinetic pump). Continuous cycles of activation/deactivation can be repeated, with each cycle delivering one of the fluid shot amounts. An example of such operation is discussed herein. Closed loop control schemes can alter one or more of the parameters discussed with respect to an activation/deactivation cycle to control delivery of the infusion fluid. For instance, the shot duration of each shot can be altered such that a selected delivery rate of infusion fluid from the pump is achieved over a plurality of activation/deactivation cycles. Alteration of shot durations during activation/deactivation cycles can be utilized advantageously for the delivery of particular infusion fluids such as insulin. For example, diabetic patients typically receive insulin in two modes: a bolus mode where a relatively large amount of insulin can be dosed (e.g., just before a patient ingests a meal), and a basal mode where a relatively smaller, constant level of insulin is dosed to maintain nominal glucose levels in the patient. By utilizing activation/deactivation cycles, both delivery modes can easily be accommodated by simply adjusting the shot duration (e.g., very short shots during basal delivery and one or more longer shots for a bolus delivery) and/or the deactivation duration.

One potential advantage to operating under repeated activation/deactivation cycles is that such an operation prevents too much infusion fluid from being released at once. Take, for example, an infusion pump operating at a constant delivery rate (i.e., not a continuous activation/deactivation cycle). If such an infusion pump becomes occluded, a closed loop controller could potentially continue to try and advance the plunger, causing the pressure to rise in the infusion set with little change in fluid delivery. Thus, if the occlusion is suddenly removed, the stored pressure could inject a potentially hazardous and even lethal dose of infusion fluid into the patient. Electrokinetic infusion pumps operating under a repeated cycle of activation and deactivation can reduce the risk of overdose by allowing the pressure stored within the infusion set to decrease over time due to leakage back through the electrokinetic porous material. Accordingly, some of the embodiments discussed herein utilize an infusion pump operating with an activation/deactivation cycle.

Another potential advantage of utilizing continuous activation/deactivation cycles is that such cycles can help an electrokinetic pump avoid potential mechanical inefficiencies. For example, with respect to insulin delivery in the basal mode, a very small pressure may be associated with infusing insulin at a slow rate. Very low pressures, however, may result in mechanical inefficiencies with pump movement. For example, smooth partition/piston movement may require a threshold pressure that exceeds the low pressure needed to infuse insulin at the designated basal rate, otherwise sporadic movement may result, leading to difficulties in pump control. By utilizing activation/deactivation cycles, a series of relatively small "microboluses" can be released, sufficiently spaced in time, to act as a virtual basal delivery. Each microbolus can use a high enough pressure to avoid the mechanical inefficiencies.

Some embodiments are directed to methods of controlling fluid delivery from an electrokinetic infusion pump. The electrokinetic infusion pump can be configured to deliver one or more fluid shot amounts. For example, the pump can deliver a single continuous fluid shot amount, consistent with continuous operation. Alternatively, a plurality of fluid shot amounts can be delivered as in a series of activation/deactivation cycles. One or more measured amounts can be determined for the plurality of shot amounts. For example, a measured amount can be obtained for each of a plurality of fluid shots, or after a selected number of fluid shots when a pump operates utilizing a series of activation/deactivation cycles. In another example, a series of measured amounts can be determined for a single continuous shot, corresponding to determining the amount of fluid displaced from the pump over a series of given time intervals during continuous fluid dispensing. Fluid shot amounts and measured amounts can be described by a variety of quantities that denote an amount of fluid. Though volume is utilized as a unit of shot amount in some embodiments, non-limiting other examples include mass, a length (e.g., with an assumption of some cross-sectional area), or a rate (e.g., volumetric flow rate, flux, etc.). An average measured amount can be calculated from the measured amounts, and subsequently used to calculate a correction factor. The correction factor can also depend upon an expected amount, which is either selected by a pump user or designated by a processor or controller of the pump. The correction factor can be used to adjust subsequent fluid delivery from the pump (e.g., used to adjust a subsequent fluid shot amount from the pump). Such subsequent fluid delivery can be used to correct for previous over-delivery or under-delivery of infusion fluid, or to deliver the expected amount.

During pump operation, as fluid is delivered, the steps of determining a measured amount; calculating an average measured amount; calculating a correction factor; and adjusting subsequent fluid delivery based at least in part on the correction factor, can be serially repeated (e.g., after each fluid shot, or after a selected plurality of fluid shots when using activation/deactivation cycles) to control dispensing of fluid from the pump. A more specific example of the implementation of these methods is described with respect to FIG. 2 herein.

Figure 2:
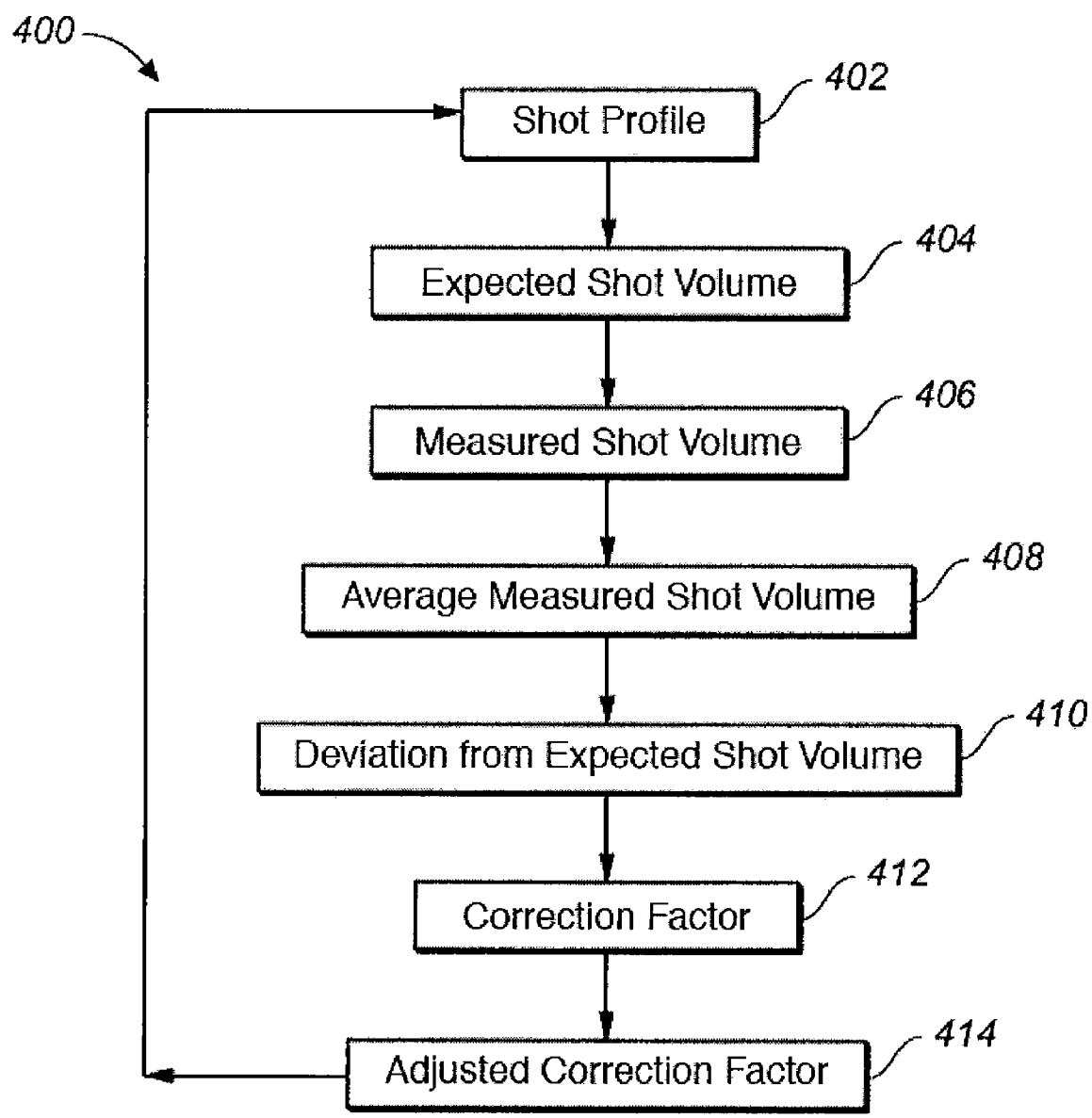
FIG. 2 is flow sheet illustrating a closed loop control algorithm for use with an electrokinetic infusion pump with closed loop control, according to an embodiment of the present invention.

FIG. 2 is a flow sheet illustrating a closed loop control algorithm 400 for use with an electrokinetic infusion pump having closed loop control, according to an embodiment of the present invention. The immediate following description herein assumes that the pump utilizes activation/deactivation cycles. Accordingly measured amounts are referred to as measured shot amounts, average measured amounts are referred to as average shot amounts, and expected amounts are referred to as expected shot amounts. It is understood, however, that the embodiment can also be utilized with a pump operating in a continuous delivery mode as described below.

With reference to FIGS. 1A, 1B, and 2, closed loop control algorithm 400 starts with an initial shot profile 402, i.e., activation of the electrokinetic pump to cause a shot of infusion fluid to be dispersed therefrom. The shot profile can be chosen to provide an expected shot fluid amount to be dispensed from the pump. In one example, shot profile 402 includes application of voltage across first electrode 110 and second electrode 112 for a selected length of time. The voltage is referred to as shot voltage, and the time is referred to as shot duration. Although one can vary shot voltage or shot duration (among other operational variables) in closed loop control algorithms, in this description, shot duration is varied.

Returning to FIG. 2, in shot profile 402, shot voltage is applied for a shot duration, resulting in a delivered amount intended to correspond with an expected shot amount. In one particular example, shot amounts are designated by volume. Therefore, the expected shot amount is an expected shot volume 404. Next a corresponding measured shot volume 406 is measured. The measured shot volume can be identified by any number of techniques. For example, by measuring the displacement of movable partition 120 during a shot profile, and knowing the cross-sectional area of a fluid reservoir, measured shot volume 406 can be determined. The displacement of the moveable partition can be determined using any number of position sensors, including those described herein.

When a position sensor is implemented, the particular technique used to measure the position of movable partition 120 can have a direct effect upon the precision and accuracy of measured shot volume 406, and, accordingly, upon closed loop control algorithm 400. In particular, if sampling of a position sensor's movement between shots is such that the actual displacement is of the order of the resolution of the position sensor, shot-to-shot precision can be difficult to maintain with a closed loop control scheme that only utilizes the last two measured shot amounts to calculate a correction factor. Other sources of error can also adversely affect the shot-to-shot precision (e.g., either random errors or systematic errors that cause a drift in an operating parameter such as fluid output over a period of time). To improve the precision and accuracy of closed loop control algorithm 400, measured shot volume 406 can be combined with previous measurements to calculate an average measured shot volume 408, which can be used in the closed loop control algorithm 400.

Returning to FIG. 2, the deviation from expected shot volume 410 can be determined by comparing the average measured shot volume 408 to the expected shot volume 404. The deviation from expected shot volume 410 can then be used to calculate a correction factor 412, which can be applied to adjust a subsequent shot profile 402. In this embodiment, the correction factor 412 is typically some value indicative of the deviation between an expected shot amount and an average shot amount. For example the correction factor 412 can be set equal to the deviation value. In another example, the correction factor 412 can be the deviation multiplied by a proportional adjustment such as a designated fraction, referred to as $\lambda$, resulting in an adjusted correction factor 414. For example, if $\lambda=0.4$, then 40 percent of deviation is applied in calculating the subsequent shot profile. Application of adjusted correction factor 414 results in a subsequent shot profile 402, and the algorithm is repeated, i.e., the adjusted correction factor is used to determine some operating pump parameter such as voltage, current, or shot duration to provide the subsequent shot profile.

In one embodiment, several measured shot volumes are determined and averaged before making corrections to shot profile 402. Henceforth, closed loop control algorithm 400 can be used to adjust shot profile 402. Closed loop control algorithm 400 can be particularly useful when electrokinetic infusion pump with closed loop control 100 is delivering infusion liquid 124 in basal mode, as is described in the Examples discussed below.

Electrokinetic Infusion Pump with Closed Loop Controller

FIG. 3 is an illustration of an electrokinetic infusion pump with closed loop control 100 according to an exemplary embodiment of the present invention. Electrokinetic infusion pump with closed loop control 100 includes closed loop controller 105 and electrokinetic infusion pump 103. In the embodiments of electrokinetic infusion pump with closed loop control 100 illustrated in FIGS. 3, 5A, 5B, 7, and 8 electrokinetic infusion pump 103 and closed loop controller 105 can be handheld, or mounted to a user by way of clips, adhesives, or non-adhesive removable fasteners. Closed loop controller 105 can be directly or wirelessly connected to remote controllers that provide additional data processing and/or analyte monitoring capabilities. As outlined earlier, and referring to FIGS. 1 and 2, closed loop controller 105 and electrokinetic infusion pump 103 can include elements that enable the position of movable partition 120 to be determined. Closed loop controller 105 includes display 140, input keys 142, and insertion port 156. After filling electrokinetic infusion pump 103 with infusion liquid 124, electrokinetic infusion pump 103 is inserted into insertion port 156. Upon insertion into insertion port 156, electrical contact is established between closed loop controller 105 and electrokinetic infusion pump 103. An infusion set is connected to the infusion reservoir outlet 123 after electrokinetic infusion pump 103 is inserted into insertion port 156, or before it is inserted into insertion port 156. Various means can be provided for priming of the infusion set, such as manual displacement of moveable partition 120 towards infusion reservoir outlet 123. After determining the position of moveable partition 120, voltage and current are applied across electrokinetic porous media 108, and infusion liquid 124 is dispensed. Electrokinetic infusion pump with closed loop control 100 can be worn on a user's belt providing an ambulatory infusion system. Display 140 can be used to display a variety of information, including infusion rates, error messages, and logbook information. Closed loop controller 105 can be designed to communicate with other equipment, such as analyte measuring equipment and computers, either wirelessly or by direct connection.

FIGS. 5A and 5B illustrate portions of an electrokinetic infusion pump with closed loop control according to an embodiment of the present invention. FIGS. 5A and 5B include electrokinetic infusion pump 103, closed loop controller 105, magnetic position sensor 176, and position sensor control circuit 160. Position sensor control circuit 160 is connected to closed loop controller 105 by way of feedback 138. Electrokinetic infusion pump 103 includes infusion housing 116, electrokinetic supply reservoir 106, electrokinetic porous media 108, electrokinetic solution receiving chamber 118, infusion reservoir 122, and moveable partition 120. Moveable partition 120 includes first infusion seal 148, second infusion seal 150, and moveable permanent magnet 149. Infusion reservoir 122 is formed between moveable partition 120 and the tapered end of infusion housing 116. Electrokinetic supply reservoir 106, electrokinetic porous media 108, and electrokinetic solution receiving chamber 118 contain electrokinetic solution 114, while infusion reservoir 122 contains infusion liquid 124. Voltage is controlled by closed loop controller 105, and is applied across first electrode 110 and second electrode 112. Magnetic position sensor 176 includes magnetostrictive waveguide 177, position sensor control circuit 160, and strain pulse detector 182. Magnetostrictive waveguide 177 and strain pulse detector 182 are typically mounted on position sensor control circuit 160.

In FIG. 5A, moveable partition 120 is in first position 168. Position sensor control circuit 160 sends a current pulse down magnetostrictive waveguide 177, and by interaction of the magnetic field created by the current pulse with the magnetic field created by moveable permanent magnet 149, a strain pulse is generated and detected by strain pulse detector 182. First position 168 can be derived from the time between initiating the current pulse and detecting the strain pulse. In FIG. 5B, electrokinetic solution 114 has been pumped from electrokinetic supply reservoir 106 to electrokinetic solution receiving chamber 118, pushing moveable partition 120 toward second position 172. Position sensor control circuit 160 sends a current pulse down magnetostrictive waveguide 177, and by interaction of the magnetic field created by the current pulse with the magnetic field created by moveable permanent magnet 149, a strain pulse is generated and detected by strain pulse detector 182. Second position 172 can be derived from the time between initiating the current pulse and detecting the strain pulse. Change in position 170 can be determined using the difference between first position 168 and second position 172. As mentioned previously, the position of moveable partition 120 can be used in controlling flow in electrokinetic infusion pump 103.

As mentioned previously, when designing an electrokinetic infusion pump with closed loop control 100, the infusion module 104 and the electrokinetic engine 102 can be integrated, as illustrated in FIGS. 3, 5A, 5B, and 7, or they can be separate components connected with tubing, as illustrated in FIG. 8. In FIG. 8, electrokinetic infusion pump with closed loop control 100 includes infusion module 104 and electrokinetic engine 102, connected by connection tubing 244. Infusion module 104 includes moveable partition 120 and infusion reservoir outlet 123. Moveable partition 120 includes moveable permanent magnet 149. Further details regarding electrokinetic engine 102, including materials, designs, and methods of manufacturing, suitable for use in electrokinetic infusion pump with closed loop control 100 are included in U.S. patent application Ser. No. 10/322,083, previously incorporated by reference.

Malfunction Detection

As indicated above, electrokinetic infusion pumps can operate in a variety of manners. For example, the pump can be configured to deliver a fluid by maintaining some operational parameter at a constant value. Non-limiting examples include flow rate of infusion fluid or electrokinetic solution, pressure, voltage or current across electrodes, and power output from a power source. In some embodiments, the pump is configured to deliver an infusion fluid by delivering a plurality of fluid shot amounts. For example, the electrokinetic infusion pump can be configured to be activated to deliver a shot amount of fluid. The amount can be determined using a variety of criteria such as a selected quantity of fluid (e.g., a microbolus of fluid) or application of a selected voltage and/or current across the electrodes of the pump for a selected period of time. Following activating, the pump can be deactivated for a selected period of time, or until some operating parameter reaches a selected value (e.g., pressure in a chamber of the electrokinetic pump). Continuous cycles of activation/deactivation can be repeated, with each cycle delivering one of the fluid shot amounts.

Figure 12:
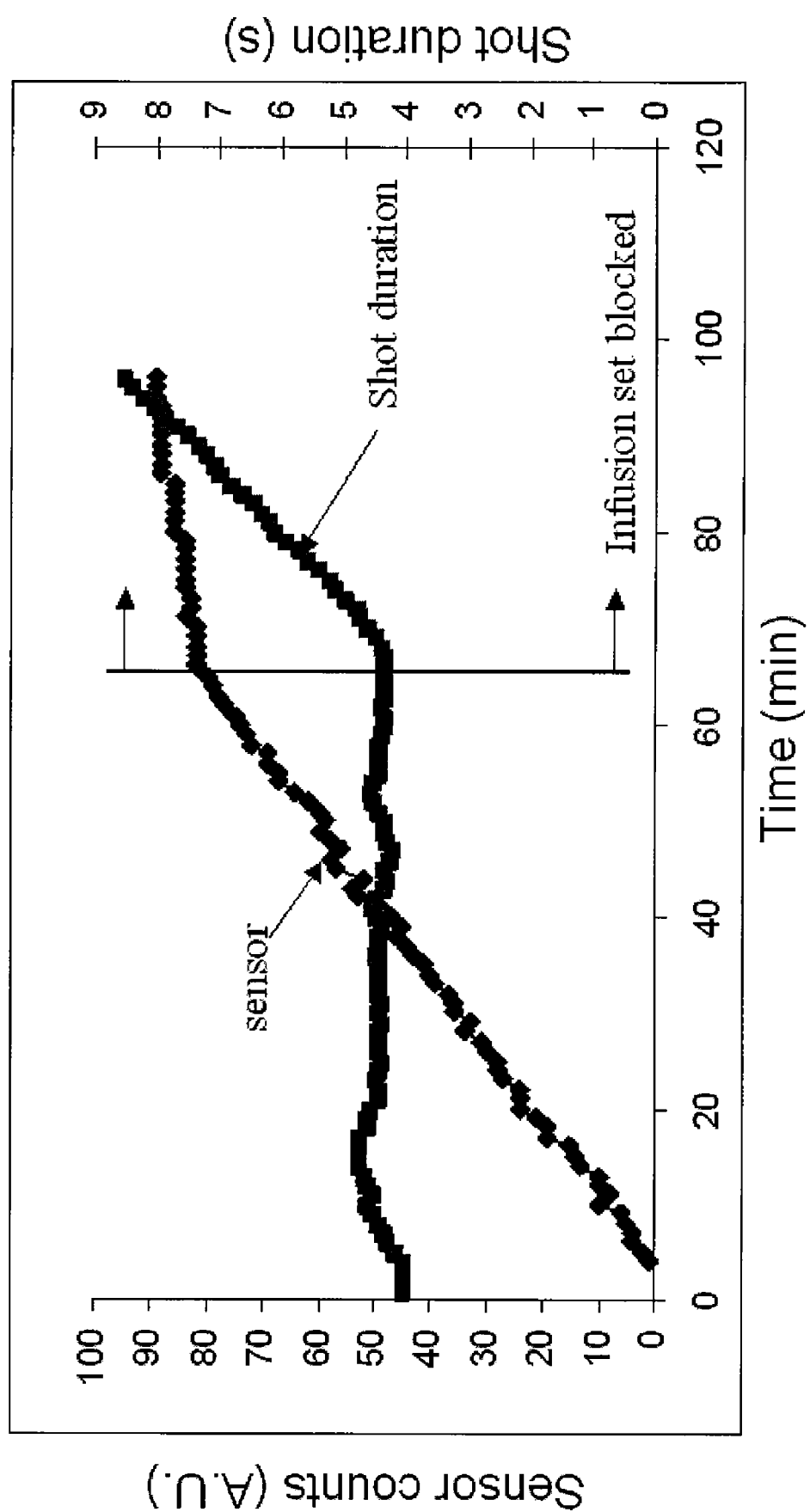
FIG. 12 is a graph illustrating sensor counts and shot duration as a function of time when an occlusion occurs in a electrokinetic infusion pump with closed loop control according to an embodiment of the present invention.

One potential advantage to operating under the continuous activation/deactivation cycle is that such an operation can prevent too much infusion fluid from being released at once. Take, for example, an infusion pump operating at a constant delivery rate (i.e., not a continuous activation/deactivation cycle). If such an infusion pump becomes occluded, the pump will continue to advance the plunger, causing the pressure to rise in the infusion set, but no infusion fluid will be delivered. Thus, if the occlusion is suddenly removed, the stored pressure will inject a potentially hazardous and even lethal dose of infusion fluid into the patient. Electrokinetic infusion pumps operating under a continuous cycle of activation and deactivation reduce the risk of overdose by allowing the pressure stored within the infusion set to decrease over time due to leakage back through the electrokinetic porous material. FIG. 12 presents data from an electrokinetic infusion pump with closed loop control that has become occluded. The sensor counts and shot duration are shown as a function of time. As illustrated in FIG. 12, the infusion set became blocked approximately 65 minutes into the simulation. Blockage is indicated by a decrease in forward plunger movement (reduced increase in sensor counts). As a result of the plunger movement being smaller than a desired value, the control algorithm tries to correct for this by increasing the shot duration. Because the infusion set was occluded, the closed loop controller was unable to correct the operation of the pump within its operational boundaries. The following method for detecting malfunctions provides an additional safeguard to electrokinetic infusion pump operation.

Malfunction Detection with Microbolus Delivery

Figure 16:
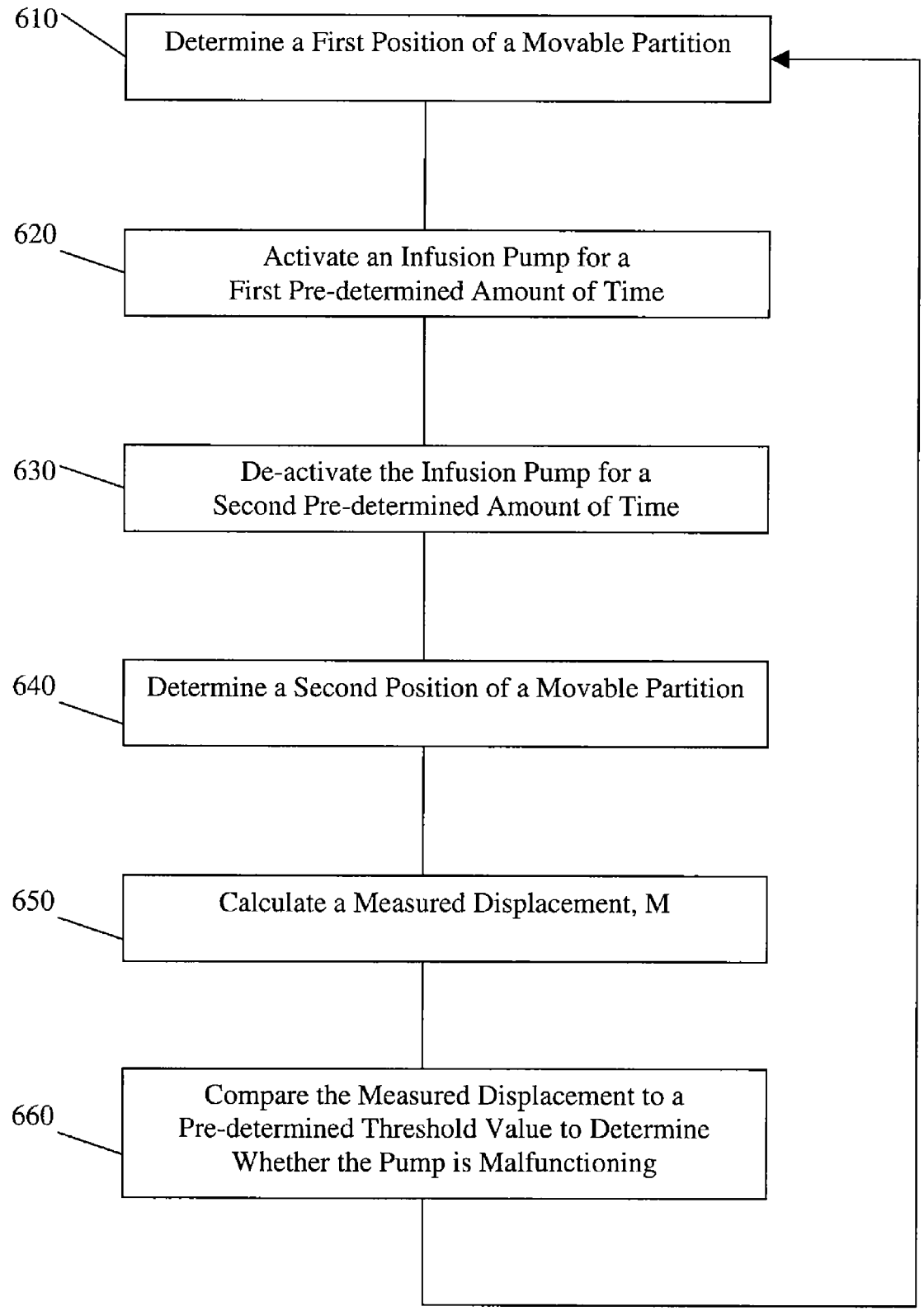
FIG. 16 is a flow sheet illustrating a malfunction detection algorithm for use with an electrokinetic infusion pump with closed loop control, according to an embodiment of the present invention.

FIG. 16 is a flow diagram illustrating an exemplary embodiment of a method of detecting malfunctions in an infusion pump with closed loop control 100. Generally, the malfunction detection method can include determining a first position of a non-mechanically driven movable partition of an infusion pump 610, activating the infusion pump to induce movement of the movable partition 620, de-activating the infusion pump 630, determining a second position of the movable partition 640, calculating a measured displacement 650 based on the first and second positions of the movable partition, and comparing the measured displacement to a pre-determined threshold value to determine whether the infusion pump is malfunctioning 660. Although the malfunction detection methods are shown and described as applied to an infusion pump having a closed loop control 100, a person skilled in the art will appreciate that the malfunction detection methods disclosed herein can be used with a variety of infusion pumps including electrokinetic infusion pumps and those pumps without closed loop control. Further, the malfunction detection methods disclosed herein are independent of any particular closed loop control algorithm and should not be limited to the closed loop control embodiments specifically discussed herein.

As shown in FIGS. 1A and 1B, the position of the movable partition 120 can be determined using a variety of techniques. For example, a position sensor associated with the closed loop controller 105 can be used to determine the position of the movable partition 120. Exemplary position sensors include, but are not limited to, magnetic position sensors, optical position sensors, or linear variable differential transformers. In a particular example, anisotropic magnetic resistive sensors can be advantageously used with infusion pumps, as described in the co-pending application entitled "Infusion Pumps with a Position Sensor", filed concurrently herewith and hereby incorporated herein by reference in its entirety. A person skilled in the art will appreciate that any sensor capable of measuring position can be used occlusion detection methods disclosed herein.

After determining the position 119 of the movable partition 120, the infusion pump can be activated for a first pre-determined amount of time to induce movement of the movable partition 120. The infusion pump can then be de-activated for a second pre-determined amount of time, and a second position 121 of the movable partition 120 can be determined. As indicated above, activating the infusion pump can include delivering a shot amount of fluid. The amount can be determined using a variety of criteria such as a selected quantity of fluid (e.g., a microbolus of fluid) or application of a selected voltage and/or current across the electrodes of the pump for a selected period of time. Following activation, the pump can be deactivated for a selected period of time, or until some operating parameter reaches a selected value (e.g., pressure in a chamber of the pump). Deactivation can include reducing or eliminating the voltage or current across the electrodes. Activating and de-activating the infusion pump for the first and second pre-determined amounts of time can affect the amount of pressure in the pump and how long it takes for pressure to build up in the pump. For example, activating the pump for the first pre-determined amount of time can be effective to cause a pressure build up in the pump such that the pressure build up is effective to induce movement of the movable partition. De-activating the pump can be effective reduce the amount of pressure in the pump. In one embodiment, the infusion pump can be de-activated for a longer period of time to cause a larger drop in pressure in the pump. In another embodiment, the infusion pump can be de-activated for a shorter period of time to cause a smaller drop in pressure in the pump. Thus, the amount of pressure in the pump can be controlled by increasing or decreasing the de-activation time. Continuous cycles of activation/deactivation can be repeated, with each cycle delivering one of the fluid shot amounts. Further, the infusion pump can be activated and/or de-activated prior to determining the position of the movable partition.

Once the first and second positions 119, 121 of the movable partition 120 are determined, a measured displacement can be calculated based on the first and second positions 119, 121 of the movable partition 120. The measured displacement can represent a variety of characteristics of pump operation. For example, in one embodiment, the measured displacement can represent the actual distance traveled by the movable partition 120. In another exemplary embodiment, the measured displacement can represent the volume of infusion fluid displaced by the movable partition 120. After calculating the measured displacement, some measure of the displacement can be compared to a pre-determined threshold value to determine whether the infusion pump is malfunctioning 660. The comparison of measured displacement to the pre-determined threshold value can take a variety of forms. For example, in one embodiment, the actual measured displacement can be compared to the pre-determined threshold value. In another embodiment, the square of the actual measured displacement can be compared to the pre-determined threshold value. In yet another exemplary embodiment, comparing the measured displacement to the pre-determined threshold value can include indicating a presence of a malfunction if an absolute value of difference between the measured displacement and the pre-determined threshold value is greater than a predetermined threshold difference.

Figure 16A:
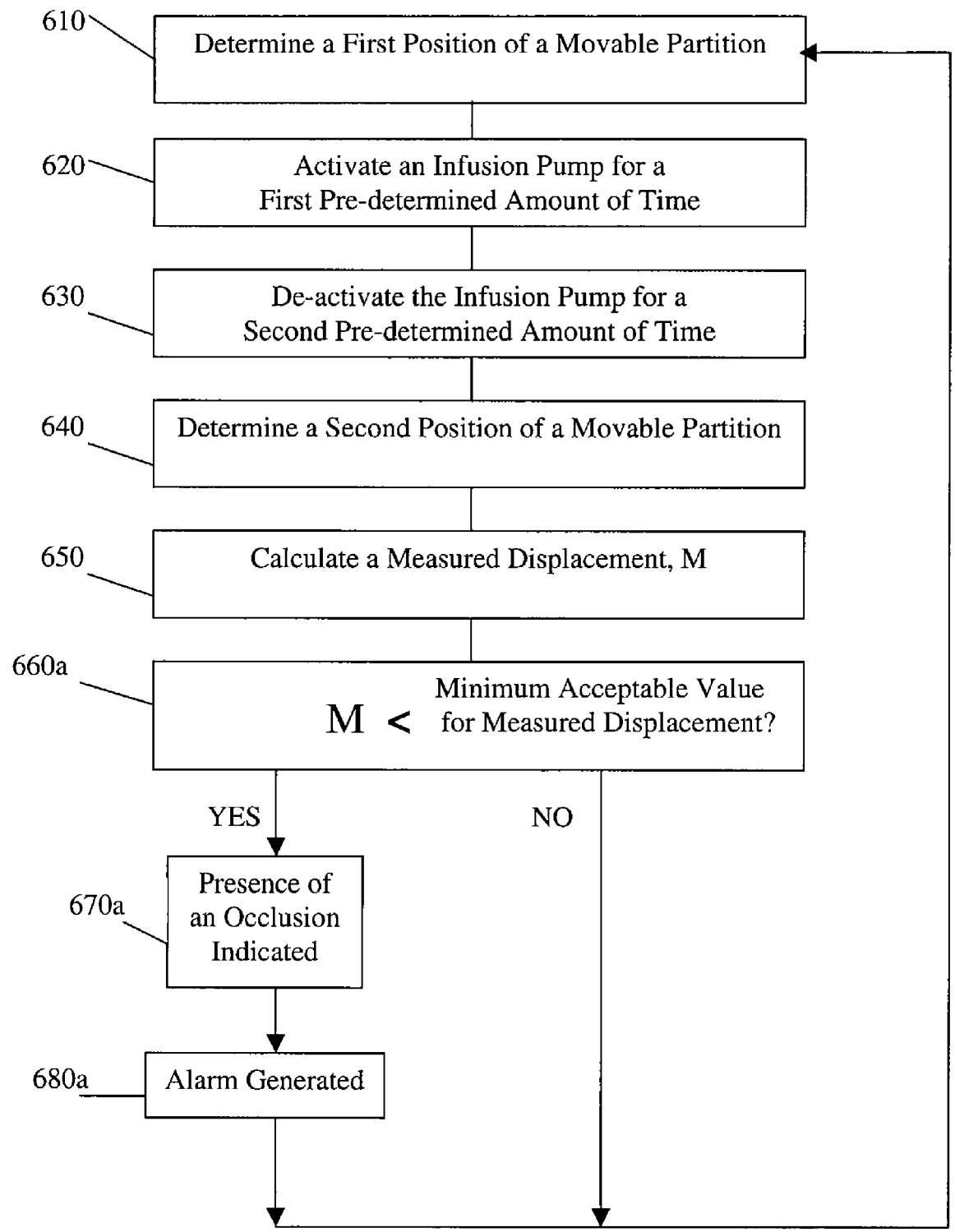
FIG. 16A is a flow sheet illustrating one embodiment of the malfunction detection algorithm shown in FIG. 16.
Figure 16B:
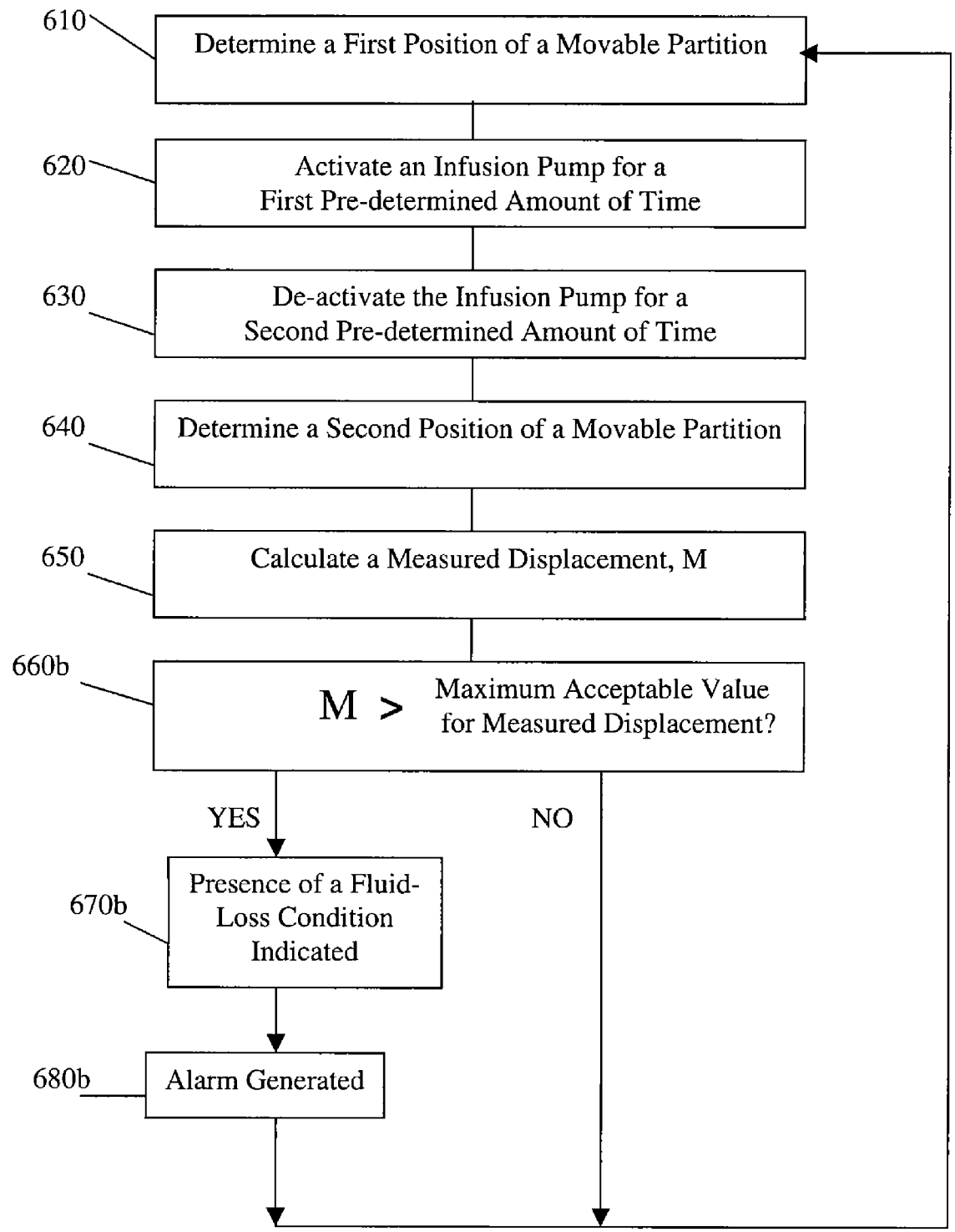
FIG. 16B is a flow sheet illustrating another embodiment of the malfunction detection algorithm shown in FIG. 16.

The pre-determined threshold value can represent a variety of infusion pump operating parameters. For example, in one exemplary embodiment shown in FIG. 16A, the pre-determined threshold value can be a minimum acceptable value for the measured displacement of the movable partition. In this embodiment, comparing the measured displacement to the pre-determined threshold value can further include indicating the presence of an occlusion in the infusion pump 670a if the measured displacement is less than the pre-determined threshold value 660a. In another exemplary embodiment, shown in FIG. 16B, the pre-determined threshold value can be a maximum acceptable value for the measured displacement of the movable partition. In this embodiment, comparing the measured displacement to the pre-determined threshold value can further include indicating the presence of a fluid-loss condition 670b (e.g., an infusion set disconnect or a leak) in the infusion pump if the measured displacement is greater than the pre-determined threshold value 660b. These pre-determined threshold values can be selected by a user or determined by a processor or controller, as described herein, depending upon a desired pump operation mode.

In one exemplary embodiment, the malfunction detection method can include two pre-determined threshold values. In this embodiment, one pre-determined threshold value can correspond to occlusion detection and the other pre-determined threshold value can correspond to fluid-loss detection. Thus, this embodiment can provide simultaneous detection of both occlusions and fluid-loss conditions. All or some of the malfunction detection steps described above can be included in this embodiment.

As indicated above, it can be advantageous to operate the infusion pump under a continuous activation/deactivation cycle. Thus, in one exemplary embodiment of the malfunction detection method disclosed herein, all or some of the above steps can be repeated so as to monitor the infusion pump for malfunctions throughout all or part of the activation/deactivation cycle. A person skilled in the art will appreciate that the steps of the method need not occur in any specific order. For example, the infusion pump can be activated prior to determining a first position of the movable partition. In an exemplary embodiment, the above steps can be repeated as the movable partition 120 is advanced through the infusion housing 116. In this embodiment, the step of determining the first position of the movable partition 120 can include equating the first position of the movable partition 120 with a partition position corresponding with a previously measured position of the movable partition. In yet another embodiment, the method can include generating an alarm if the presence of a malfunction is detected 680a, 680b.

Figure 18:
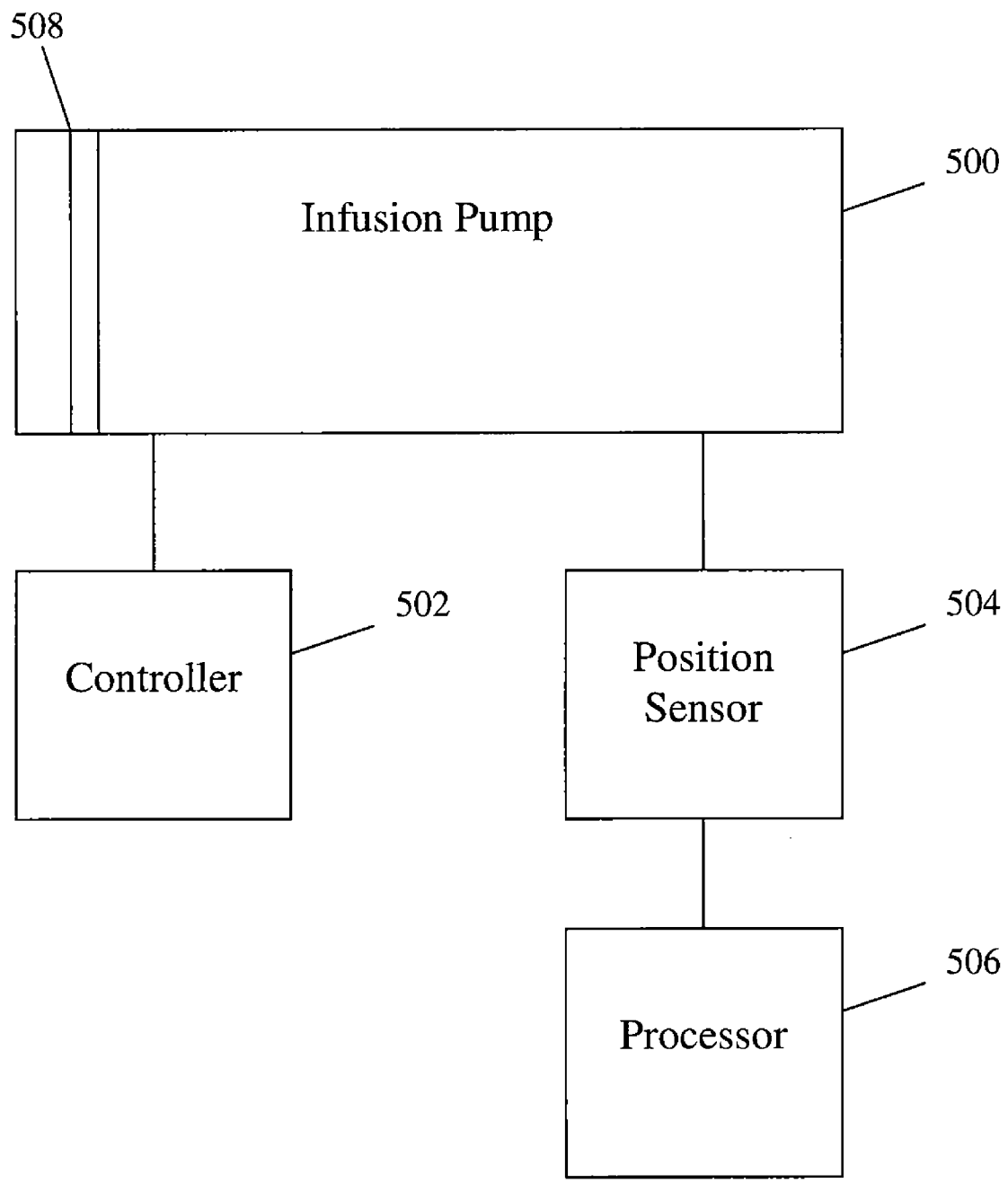
FIG. 18 illustrates a malfunction detection system according to an embodiment of the present invention.

A system for detecting a malfunction in an infusion pump is also provided. As shown in FIG. 18, the system can include an infusion pump 500 having a non-mechanically driven movable partition 508 (e.g., hydraulically actuated) disposed therein, a position sensor 504 disposed on the pump 500, a controller 502 associated with the pump 500, and a processor 506 associated with the position sensor 504. In one exemplary embodiment, the infusion pump can be an electrokinetic infusion pump. A variety of configurations are available for the position sensor 504. For example, the position sensor can be a magnetic sensor, an optical sensor, or a linear variable differential transformer. A person skilled in the art will appreciate that any sensor adapted to measure position can be used with the malfunction detection system.

The controller 502 of the malfunction detection system can be adapted to operate the infusion pump 500 in an activate/de-activate cycle. The cycle can include activating the pump 500 for a first pre-determined amount of time to induce movement of the movable partition 508 and de-activating the pump 500 for a second pre-determined amount of time. The controller 502 can also be adapted to cause a pressure build up in the infusion pump 500 as the pump 500 is activated and de-activated for the first and second pre-determined amounts of time. In one exemplary embodiment, the controller 502 can be adapted to repeat the activate/de-activate cycle while fluid is being delivered by the infusion pump 500. A person skilled in the art will appreciate that the controller 502 can be adapted to repeat the cycle as many times are as necessary for the movable partition 508 to proceed through the infusion pump 500. Furthermore, one or more separate components or hardware control units can be combined as a "controller" consistent with embodiments of the invention described herein. As well, a "controller" can include memory units that are read-only or capable of being overwritten to hold parameters such as selected values or control parameters (e.g., the number of measured shot amounts used in an averaging calculating, an expected shot amount, the first and second pre-determined amounts of time, etc.). All these variations, and others, are within the scope of the disclosure of the present application.

The processor 506 of the malfunction detection system can be adapted to calculate a measured displacement based on the first and second positions of the movable partition 508 and to compare the measured displacement with a pre-determined threshold value to determine whether the infusion pump 500 is malfunctioning. The processor 506 can also be adapted to lengthen or shorten the amount of time that the pump 500 is de-activated to cause a slower or faster build-up of pressure in the pump, respectively. In one embodiment, the processor 506 can be adapted to indicate a presence of a malfunction if an absolute value of difference between the measured displacement and the pre-determined threshold value is greater than a predetermined threshold difference. As indicated above, the pre-determined threshold value can represent a variety of infusion pump operating parameters. For example, in one exemplary embodiment, the pre-determined threshold value can be a minimum acceptable value for the measured displacement of the movable partition. In this embodiment, the processor 506 can be configured to indicate the presence of an occlusion in the infusion pump if the measured displacement is less than the pre-determined threshold value. In another exemplary embodiment, the pre-determined threshold value can be a maximum acceptable value for the measured displacement of the movable partition. In this embodiment, the processor 506 can be configured to indicate the presence of a fluid-loss condition in the infusion pump if the measured displacement is greater than the pre-determined threshold value. In one exemplary embodiment, the system can further include an alarm adapted to receive a signal from the processor 506 and to indicate the presence of a malfunction.

In another exemplary embodiment, the malfunction detection system can include two pre-determined threshold values. One pre-determined threshold value can correspond to occlusion detection and the other pre-determined threshold value can correspond to fluid-loss detection. Thus, this embodiment can provide simultaneous detection of both occlusions and fluid-loss conditions. In this embodiment, the processor can be configured to indicate the presence of an occlusion if the calculated moving average is less than a pre-determined occlusion threshold value as well as indicate the presence of a fluid-loss condition if the calculated moving average is greater than a pre-determined fluid-loss threshold value. Additionally, in this embodiment, the processor can include all the functionality as described above.

Furthermore, as with the controller 502 described above, one or more separate components or hardware/software control units can be combined as a "processor" consistent with embodiments of the invention described herein. As well, a "processor" can include memory units that are read-only or capable of being overwritten to hold parameters such as selected or pre-determined values or control parameters (e.g., the measured displacement, the expected displacement, the first and second pre-determined amounts of time, etc.). All these variations, and others, are within the scope of the disclosure of the present application.

Malfunction Detection with Derivative Calculation

Figure 17:
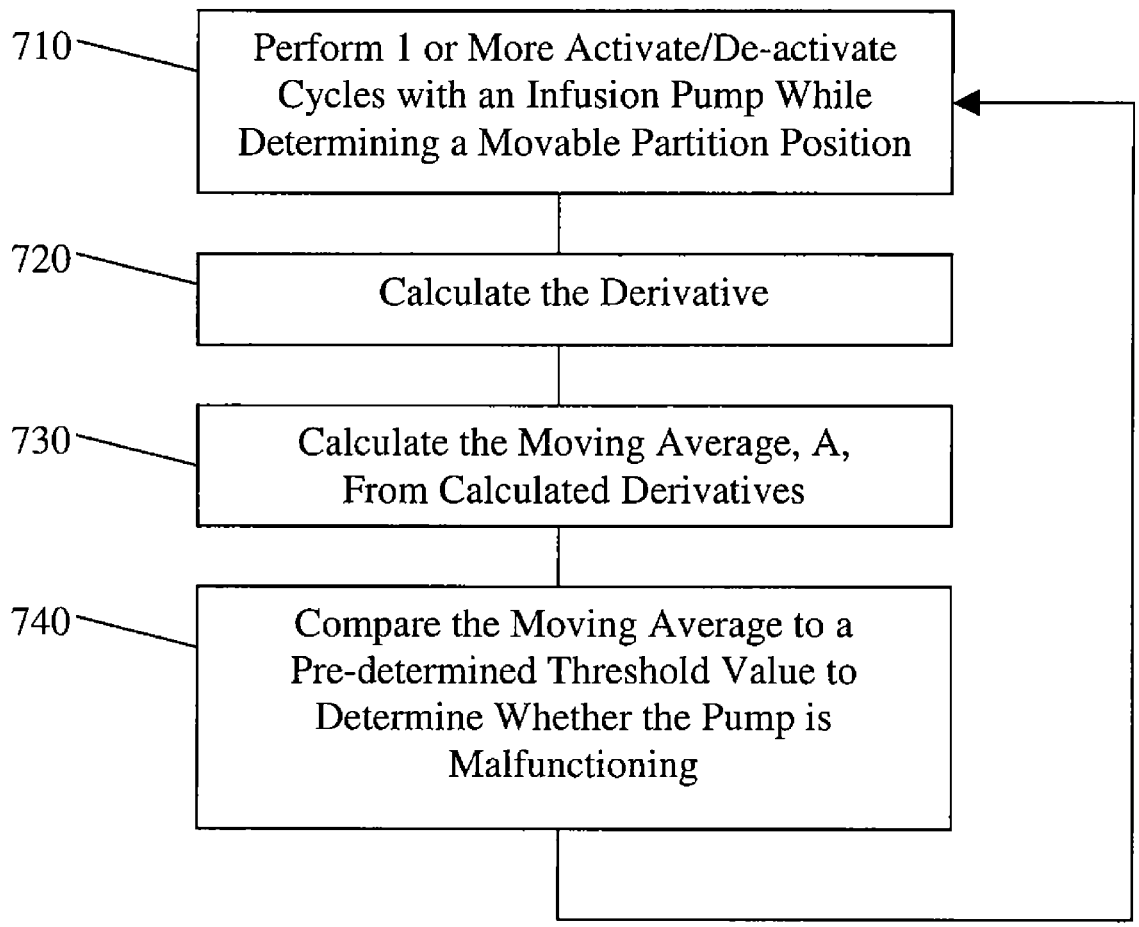
FIG. 17 is a flow sheet illustrating another malfunction detection algorithm for use with an electrokinetic infusion pump with closed loop control, according to an embodiment of the present invention.

Another exemplary embodiment of a method for detecting a malfunction in an infusion pump is illustrated in general form in the flow chart provided in FIG. 17. The infusion pump can be activated 710 for a first pre-determined amount of time to induce movement of a non-mechanically driven movable partition of the pump and to release a shot of fluid from the pump. In an exemplary embodiment, the infusion pump can be an electrokinetic infusion pump. The infusion pump can then be de-activated 710 for a second pre-determined amount of time, and the position of the movable partition can be determined 710 using any of the techniques described above, for example, using a magnetic sensor. The above steps can then be repeated for each of a plurality of instances 710. For example, the above steps can be repeated for at least two, three, or five instances. A person skilled in the art will appreciate that the above steps can be repeated for any number of plurality of instances. Note that the position of the movable partition need not be determined at the end of each activate/de-activate cycle. In some embodiments, the activate-de-activate cycle can be run for a selected number of times before determining the position of the movable partition.

A derivative for each of the plurality of instances can then be calculated 720. The derivative can be based on a change in position of the movable partition with respect to a change in the number of shots intended to be released. The change in position of the movable partition can be represented by a variety of parameters. For example, in one embodiment, the change in position can represent the actual measured distance traveled by the movable partition. In another embodiment, the change in position can be represented by a change in sensor counts (e.g., a change in position sensor output). Additionally, in an exemplary embodiment, the derivative can be calculated using the last two known positions of the movable partition for each of the plurality of instances. A person skilled in the art will appreciate that the derivative can be calculated using any two known positions of the movable partition for each of the plurality of instances.

After calculating the derivative, a moving average can be calculated using the calculated derivative values corresponding to each of the plurality of instances 730. In an exemplary embodiment, the moving average can represent the average of the last N calculated derivative values over a specified period of time, number of activate/de-activate cycles, or number of shots released. In one embodiment, calculating the moving average can further include multiplying the calculated derivative values by a weighting factor. In another embodiment, the moving average can be an arithmetic mean of derivative values. The calculated moving average can then be compared with a pre-determined threshold value to determine whether the infusion pump is malfunctioning 740.

Figure 13:
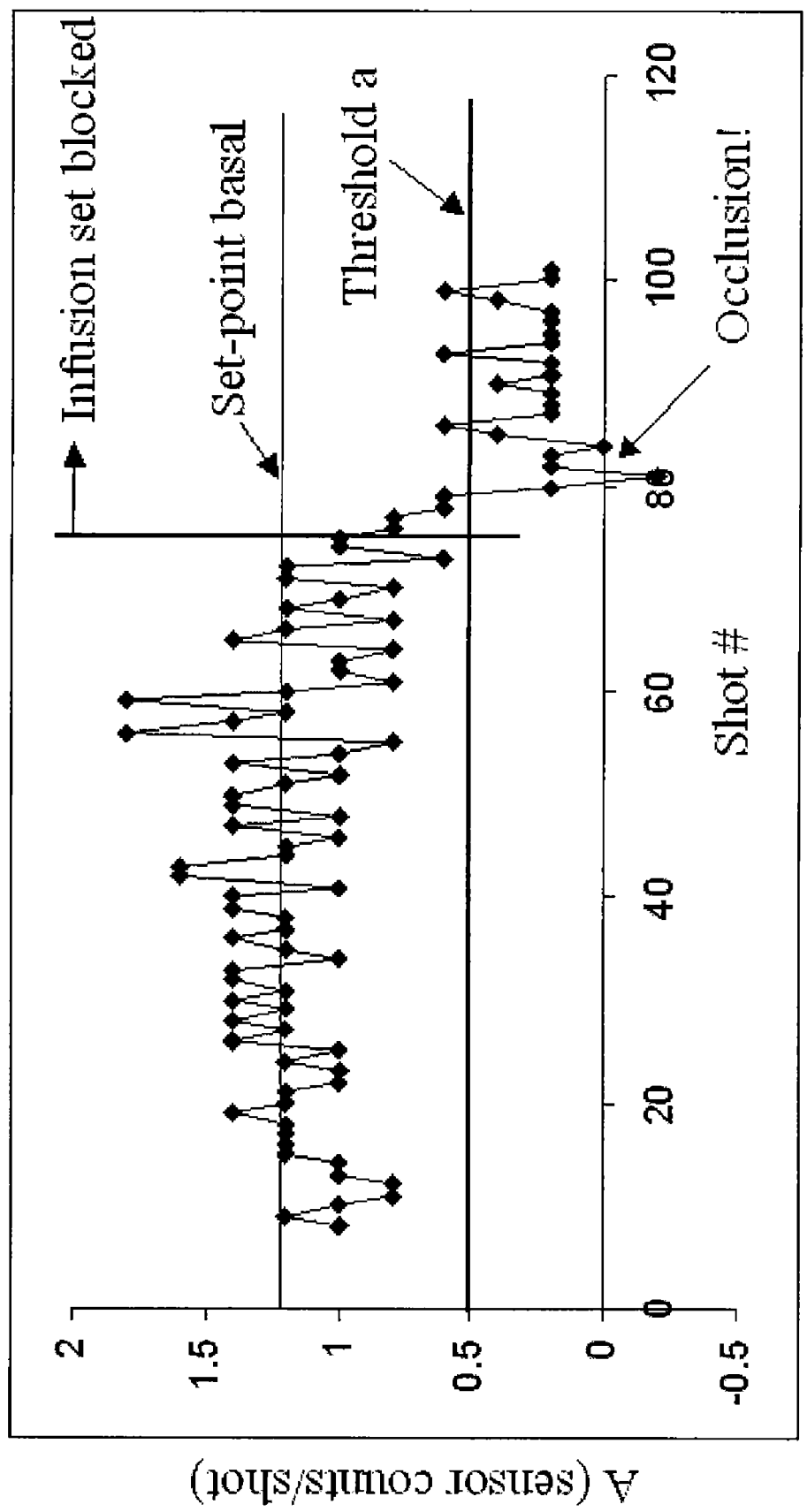
FIG. 13 is graph illustrating the moving average over the course of a series of shots when an occlusion occurs in a electrokinetic infusion pump with closed loop control according to an embodiment of the present invention.
Figure 17A:
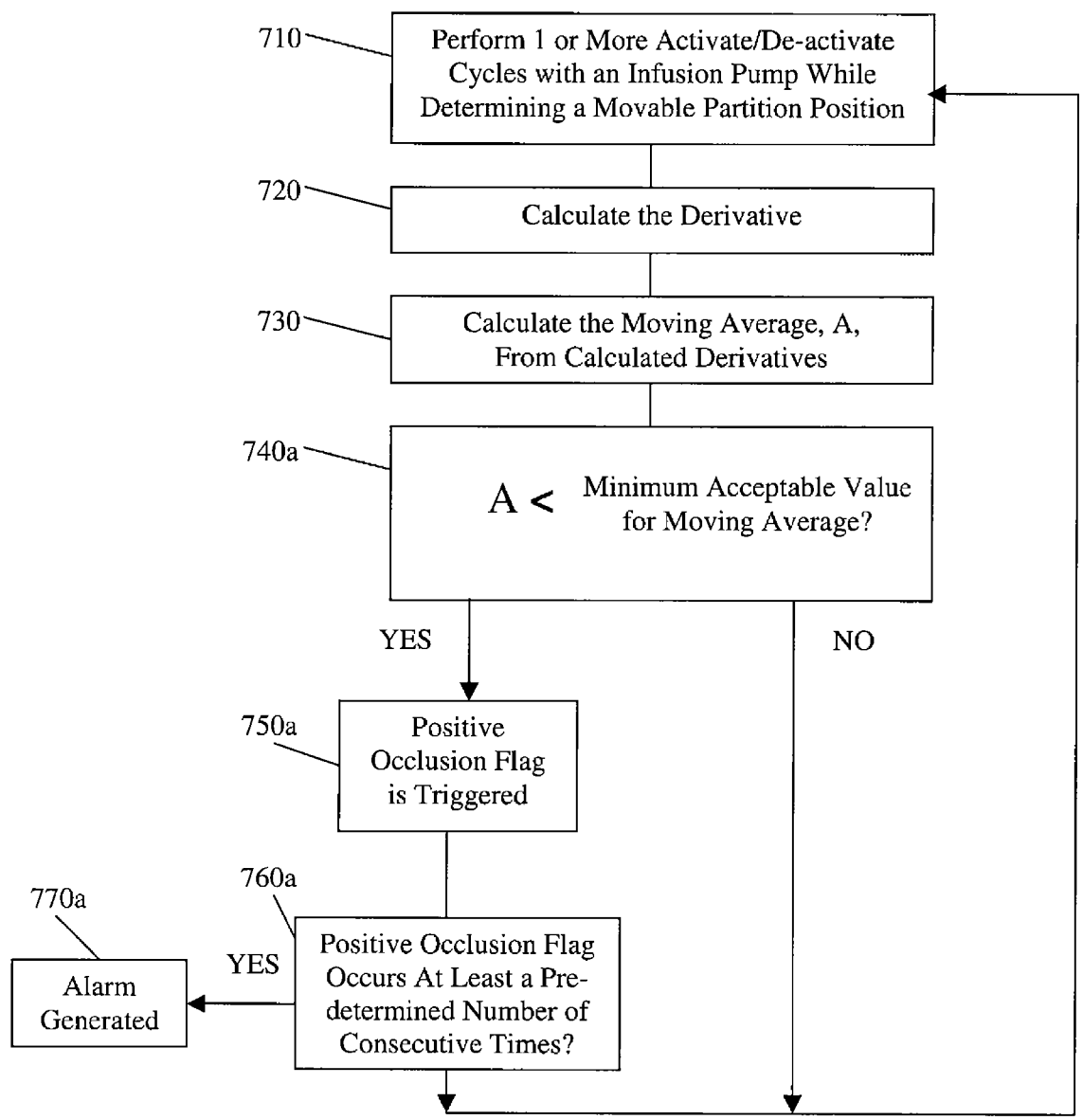
FIG. 17A is a flow sheet illustrating one embodiment of the malfunction detection algorithm shown in FIG. 17.

The pre-determined threshold values can be selected by a user or determined by a processor or controller, as described herein, depending upon a desired pump operation mode. Moreover, the pre-determined threshold values can represent a variety of infusion pump operating parameters. For example, in one exemplary embodiment shown in FIG. 17A, the predetermined threshold value can represent a minimum acceptable value for the change in position of the movable partition with respect to the change in the number of shots released 740a. In other words, if the change in position of the movable partition with respect to the change in number of shots released is less than the pre-determined threshold value, this can indicate that the proper amount of infusion fluid is not being released (i.e., too little infusion fluid is released) and that the pump may be occluded. FIG. 13 illustrates the moving average A (sensor counts/shot) over the course of a series of shots, wherein the moving average A is an average of calculated derivative values based on a change in position of a movable partition of a pump with respect to a change in the number of shots released by the pump. As shown in FIG. 13, the algorithm indicated a malfunction (i.e., an occlusion) in the infusion pump after approximately 80 shots when the moving average A dropped below threshold a which was set at 0.5 sensor counts/shot. In one exemplary embodiment, comparing the calculated moving average to the pre-determined threshold value can further include triggering a positive occlusion flag if the calculated moving average is less than the pre-determined threshold value 750a. Further, the occurrence of a positive occlusion flag can also include generating an alarm signal if the calculated moving average is less the first pre-determined threshold value 770a.

As indicated above, it is advantageous to operate the infusion pump under a continuous activation/deactivation cycle. Thus, in one exemplary embodiment of the malfunction detection method disclosed herein, all or some of the above steps can be repeated so as to monitor the infusion pump for malfunctions throughout all or part of the activation/deactivation cycle. For example, the above steps can be repeated as the movable partition 120 is advanced through the infusion housing 116. In this embodiment, the step of comparing the calculated moving average can include indicating the presence of an occlusion if the positive occlusion flag occurs at least a pre-determined number of consecutive times 760a. Some non-limiting examples of pre-determined number of consecutive times include at least two, three, or five consecutive positive occlusion flags. A person skilled in the art will also appreciate that the pre-determined number of consecutive times can be any number of times and determination of which will depend on the infusion pump's individual design and operating parameters.

Figure 15:
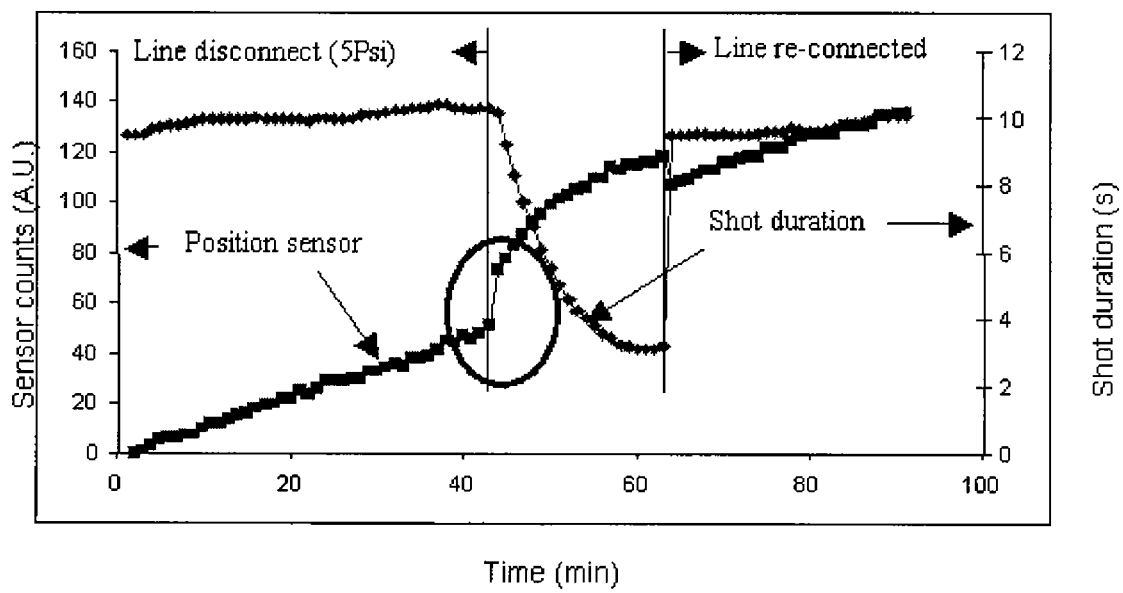
FIG. 15 is a graph illustrating sensor counts and shot duration as a function of time when a disconnect occurs in a electrokinetic infusion pump with closed loop control according to an embodiment of the present invention.
Figure 17B:
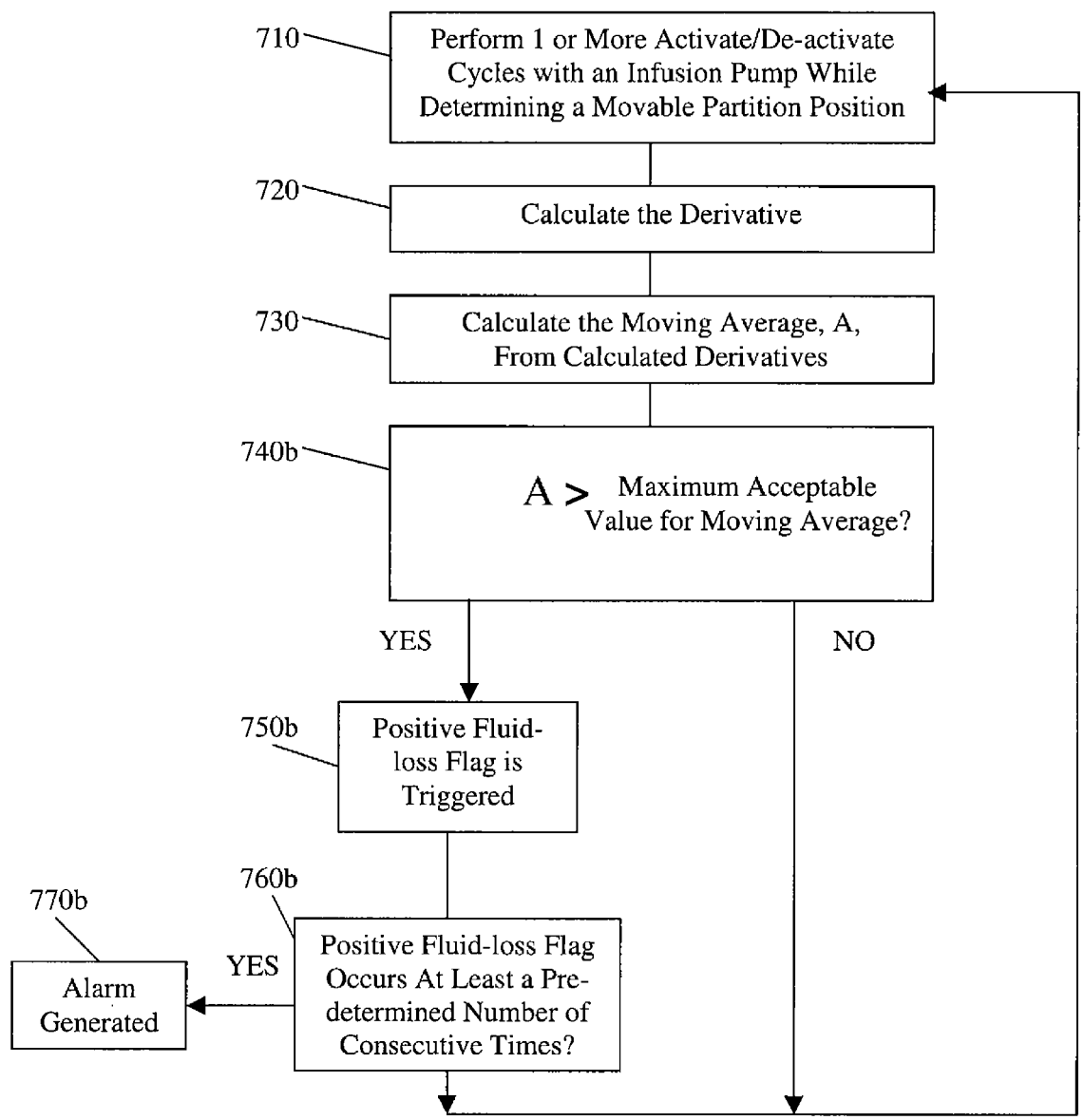
FIG. 17B is a flow sheet illustrating another embodiment of the malfunction detection algorithm shown in FIG. 17.

As shown in FIG. 17B, the pre-determined threshold value can also represent a maximum acceptable value for the change in position of the movable partition with respect to the change in the number of shots released 740b. In other words, if the change in position of the movable partition with respect to the change in number of shots released is greater than the pre-determined threshold, this can indicate that the proper amount of infusion fluid is not being released (i.e., too much infusion fluid is released) and that there may be a fluid-loss condition in the infusion set (e.g., an infusion set disconnect or a leak). FIG. 15 presents data from an electrokinetic infusion pump with closed loop control having a fluid-loss condition in the infusion set. The sensor counts and shot duration are shown as a function of time. As shown in FIG. 15, a malfunction was detected at approximately 45 minutes into the experiment. At this time, the infusion set was disconnect from the infusion reservoir, resulting in a lowering of infusion pressure as the hydraulic resistance in the infusion line was removed. This reduction of pressure results in a noticeable sudden forward movement of the plunger. As a result of the increased speed of the plunger, the control algorithm reduced the shot duration. The fluid-loss condition is indicated by a decrease in shot duration and an increase in sensor counts, as the closed loop control attempted to correct the malfunctioning electrokinetic infusion pump. As indicated in FIG. 15, the line was reconnected at approximately 65 minutes into the experiment and it can be seen that the control algorithm increased the shot duration to accommodate the increased backpressure due to the re-attachment of the infusion line. In one exemplary embodiment, comparing the calculated moving average to the pre-determined threshold value can further include triggering a positive fluid-loss flag if the calculated moving average is greater than the pre-determined threshold value 750b. Further, the occurrence of a positive fluid-loss flag can also include generating an alarm signal if the calculated moving average is greater the first pre-determined threshold value 770b.

In one exemplary embodiment, the malfunction detection method can include two pre-determined threshold values. In this embodiment, one pre-determined threshold value can correspond to occlusion detection and the other pre-determined threshold value can correspond to fluid-loss (or set disconnect) detection. Thus, this embodiment can provide simultaneous detection of both occlusions and fluid-loss conditions. All or some of the malfunction detection steps described above can be included in this embodiment.

As indicated above, it is advantageous to operate the infusion pump under a continuous activation/deactivation cycle. Thus, similar to the occlusion detection method, all or some of the above steps can be repeated so as to monitor the infusion pump for fluid-loss conditions throughout all or part of the activation/deactivation cycle. As with the occlusion detection method, the step of comparing the calculated moving average can include indicating the presence of a fluid-loss condition if the positive fluid-loss flag occurs at least a pre-determined number of consecutive times 760b. Some non-limiting examples of pre-determined number of consecutive times include at least two, three, or five consecutive positive fluid-loss flags. One skilled in the art will appreciate that the pre-determined number of consecutive times need not be the same for indicating the presence of an occlusion and/or a fluid-loss condition. For example, the presence of an occlusion can be indicated if the positive occlusion flag occurs at least three times, and the presence of a fluid-loss condition can be indicated if the positive fluid-loss flag occurs at least two times. A person skilled in the art will also appreciate that the methods disclosed herein for detecting occlusions and/or fluid-loss conditions can be performed independent of each other or in conjunction.

A system associated with the above method for detecting a malfunction in an infusion pump is also provided. The system can include an infusion pump 500 having a non-mechanically driven movable partition 508 disposed therein, a position sensor 504 disposed on the pump 500, a controller 502 associated with the pump 500, and a processor 506 associated with the position sensor 504. In one exemplary embodiment, the infusion pump can be an electrokinetic infusion pump. A variety of configurations are available for the position sensor 504. For example, the position sensor 504 can be a magnetic sensor, an optical sensor, or a linear variable differential transformer. A person skilled in the art will appreciate that any sensor adapted to measure position can be used with the malfunction detection system.

The controller 502 of the malfunction detection system can be adapted to operate the infusion pump 500 in an activate/de-activate cycle. The cycle can include activating the pump for a first pre-determined amount of time to induce movement of the movable partition and release a shot of fluid and de-activating the pump for a second pre-determined amount of time. The controller 502 can also be adapted to cause a pressure build up in the infusion pump 500 as the pump is activated and de-activated for the first and second pre-determined amounts of time. In one exemplary embodiment, the controller 502 can be adapted to repeat the activate/de-activate cycle while fluid is being delivered by the infusion pump 500. A person skilled in the art will appreciate that the controller 502 can be adapted to repeat the cycle as many times are as necessary for the movable partition 508 to proceed through the infusion pump 500.

Figure 14:
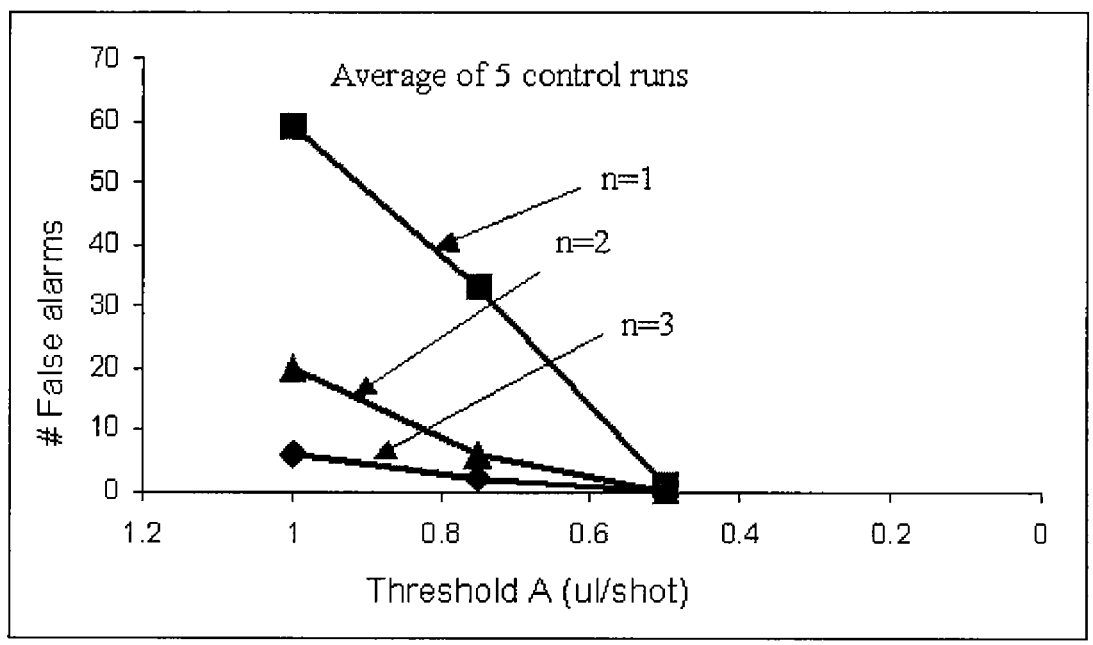
FIG. 14 is a graph illustrating the number of false alarms for various values of first pre-determined threshold values.

The processor 506 of the malfunction detection system can be adapted to perform a series of functions after each activate/de-activate cycle. For example, the processor 506 can be adapted to calculate a derivative based on a change in position of the movable partition 508 with respect to a change in the number of shots released. The processor 506 can also be adapted to calculate a moving average from a plurality of the calculated derivative values. In one exemplary embodiment, calculating the moving average can further include multiplying the calculated derivative values by a weighting factor. The processor 506 can also be configured to calculate the moving average based upon calculated derivatives from at least a last three cycles. In another embodiment, the processor 506 can be configured to calculate the moving average based upon calculated derivatives from a last fives cycles. Additionally, the processor 506 can be adapted to determine whether the pump 500 is malfunctioning by comparing the calculated moving average to a pre-determined threshold value. The pre-determined threshold value can represent a variety of infusion pump operating parameters. For example, in one exemplary embodiment, the pre-determined threshold value can represent a minimum acceptable value for the change in position of the movable partition with respect to the change in the number of shots released. In this embodiment, the processor 506 can be configured to provide a positive occlusion flag if the calculated moving average is less than the pre-determined threshold value. In one embodiment, the processor 506 can be further configured to produce an occlusion detection signal if the positive occlusion flag is produced after each of at least a pre-determined number of consecutive cycles. For example, in some exemplary embodiments, the pre-determined number of cycles can be at least one, two, three, or five. FIG. 14 illustrates the number of false alarms (i.e., the number of false indications of an occlusion) for various values of pre-determined threshold values which represented the minimum acceptable value for the change in position of the movable partition with respect to the change in the number of shots released. The processor 506 used in the simulation was configured to produce an occlusion detection signal if a positive occlusion flag was produced after each or at least one, two, or three consecutive cycles. As shown in FIG. 14, the greatest number of false alarms occurred when the processor 506 was configured to produce an occlusion detection signal if a positive occlusion flag was produced after one consecutive cycle. The least number of false alarms occurred when the processor 506 was configured to produce an occlusion detection signal if a positive occlusion flag was produced after three consecutive cycles. Thus, increasing the number of consecutive positive occlusion flag cycles required before indicating the presence of an occlusion, decreases the number of false alarms. However, increasing the number of consecutive positive occlusion flag cycles required also increases the amount of time it takes to detect an occlusion.

In another exemplary embodiment, the pre-determined threshold value can represent a maximum acceptable value for the change in position of the movable partition with respect to the change in the number of shots released. In this embodiment, the processor 506 can be configured to provide a positive fluid-loss flag if the calculated moving average is greater than the pre-determined threshold value. As with the occlusion detection signal, the processor 506 can be further configured to produce an fluid-loss detection signal if the positive fluid-loss flag is produced after each of at least a pre-determined number of consecutive cycles. As indicated above, one skilled in the art will appreciate that the predetermined number of consecutive times need not be the same for indicating the presence of an occlusion and/or a fluid-loss condition. For example, the presence of an occlusion can be indicated if the positive occlusion flag occurs at least three times, and the presence of a fluid-loss condition can be indicated if the positive fluid-loss flag occurs at least two times. A person skilled in the art will also appreciate that the pre-determined number of consecutive times can be any number of times and determination of which will depend on the infusion pump's individual design and operating parameters. Additionally, in one exemplary embodiment, the system can further include an alarm coupled to the processor and adapted to produce a signal indicating a malfunction (e.g. an occlusion and/or a fluid-loss condition) upon activation.

In one exemplary embodiment, the malfunction detection method can include two pre-determined threshold values. One pre-determined threshold value can correspond to occlusion detection and the other pre-determined threshold value can correspond to fluid-loss detection. Thus, this embodiment can provide simultaneous detection of both occlusions and fluid-loss conditions. In this embodiment, the processor can be configured to provide a positive occlusion flag if the calculated moving average is less than a pre-determined occlusion threshold value as well as provide a positive fluid-loss flag if the calculated moving average is greater than a pre-determined fluid-loss threshold value. Further, in this embodiment, the processor can include all the functionality as described above.

EXAMPLES

The following examples are provided to illustrate some aspects of the present application. The examples, however, are not intended to limit the scope of any embodiment of the invention.

Example 1:

Basal and Bolus Liquid Delivery

Figure 7:
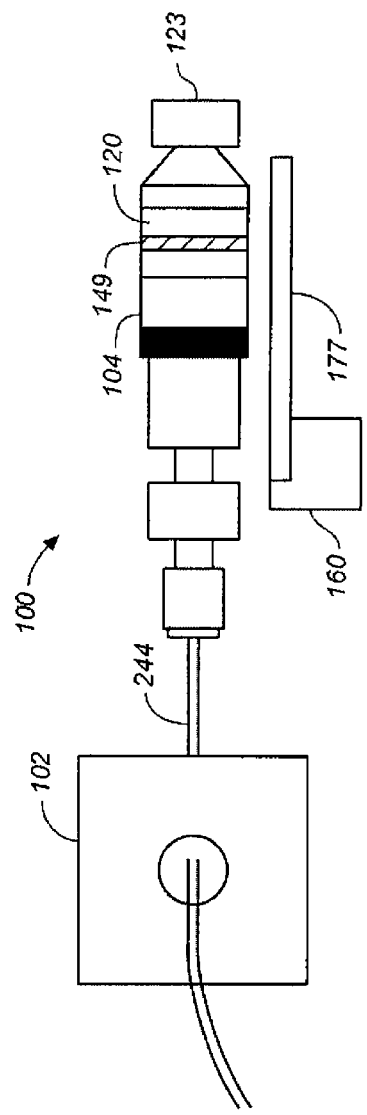
FIG. 7 is an illustration of an electrokinetic infusion pump with closed loop control according to an embodiment of the present invention. The electrokinetic infusion pump with closed loop control illustrated in FIG. 7 includes an electrokinetic engine and infusion module, and was used to generate basal and bolus delivery of infusion liquid.

Referring to FIG. 7, using an electrokinetic infusion pump with closed loop control 100 basal and bolus infusion liquid delivery rates were determined. In basal infusion, small volumes are dispensed at high frequency. In bolus infusion, large volumes are dispensed at a low frequency. Basal and bolus infusion liquid delivery rates were determined by applying voltage to electrokinetic engine 102 for a period of time (referred to as the pump on time), then switching the voltage off for a period of time (referred to as the pump off time). The sum of pump on time and pump off time is referred to as cycle time in this example. The mass of infusion liquid pumped during each cycle time (referred to as the shot size) was determined with a Mettler Toledo AX205 electronic balance. The shot size was determined repeatedly, using the same pump on time and the same cycle time, giving an indication of shot size repeatability. Using the density of water (about 1 gram per cubic centimeter), the shot size volume was derived from the mass of infusion liquid pumped during each cycle time.

Electrokinetic engine 102 was connected to infusion module 104 using connection tubing 244. Connection tubing 244 was rigid PEEK tubing with an inside diameter of .040", an outside diameter of .063", and a length of approximately 3". A similar piece of PEEK tubing, approximately 24" long, was connected to infusion reservoir outlet 123 on one end, and to glass capillary tubing on the other end. The glass capillary tubing had an inside diameter of .021", an outside diameter of .026", and a length of about 6". The end of the glass capillary tubing, which was not connected to infusion reservoir outlet 123, was inserted into a small vial being weighed by the Mettler Toledo AX205 electronic balance. A small amount of water was placed in the bottom of the small vial, covering the end of the glass capillary tubing, and a drop of oil was placed on top of the water in the bottom of the small vial to reduce evaporation of the water. Electrokinetic engine 102 was also connected to a vented electrokinetic solution reservoir (not shown in FIG. 7) that provided electrokinetic solution to electrokinetic engine 102. Electrokinetic engine 102, vented electrokinetic solution reservoir, infusion module 104, connection tubing 244, the glass capillary tubing, and the Mettler Toledo AX205 electronic balance, were placed inside a temperature-controlled box, held to +/−1° C., to eliminate measurement errors associated with temperature variations. The temperature-controlled box was placed on top of a marble table to reduce errors from vibration. A personal computer running LabView software controlled electrokinetic infusion pump with closed loop control 100 and collected data from the Mettler Toledo AX205 electronic balance.

To determine basal delivery of infusion liquid, electrokinetic engine 102 was connected to infusion module 104 with connection tubing 244 and driven with a potential of 75V. At 75V, electrokinetic engine 102 delivered electrokinetic solution to infusion module 104 at a rate of approximately 15 microliters/minute. Electrokinetic engine 102 was run with an on time of approximately 2 seconds and an off time of approximately 58 seconds, resulting in a cycle time of 60 seconds and a shot size of approximately .5 microliters. The on-time of electrokinetic engine 102 was adjusted, based upon input from magnetostrictive waveguide 177 and position sensor control circuit 160, which ran a closed loop control algorithm in accord with the description of FIG. 2. For each cycle of basal delivery, the position of moveable permanent magnet 149 was determined. If moveable permanent magnet 149 did not move enough, the on time for the next cycle of basal delivery was increased. If moveable permanent magnet 149 moved too much, the on time for the next cycle of basal delivery was decreased. The determination of position of moveable permanent magnet 149, and any necessary adjustments to on time, was repeated for every cycle of basal delivery.

To determine bolus delivery of infusion liquid, electrokinetic engine 102 was connected to infusion module 104 with connection tubing 244 and driven with a potential of 75V. Once again, at 75V electrokinetic engine 102 delivered electrokinetic solution to infusion module 104 at a rate of approximately 15 microliters/minute. Electrokinetic engine 102 was run with an on time of approximately 120 seconds and an off time of approximately 120 seconds, resulting in a cycle time of 4 minutes and a shot size of approximately 30 microliters. For each cycle of bolus delivery, the position of moveable permanent magnet 149 was determined while the electrokinetic engine 102 was on. Once moveable permanent magnet 149 moved the desired amount, electrokinetic engine 102 was turned off. The position of moveable permanent magnet 149 was used to control on time of electrokinetic engine 102 for every cycle of bolus delivery.

Basal and bolus delivery of infusion liquid were alternated, as follows. Thirty cycles of basal delivery was followed by one cycle of bolus delivery. Then, thirty-seven cycles of basal delivery, was followed by one cycle of bolus delivery. Finally, thirty-eight cycles of basal delivery was followed by a one cycle of bolus delivery and forty-nine additional cycles of basal delivery. FIG. 8 is a graph showing measured shot size as a function of time, for alternating basal delivery 243 and bolus delivery 245, as outlined above. In basal mode, the average shot size was about .5 microliters with a standard deviation of less than 2%.

Example 2:

Occlusion Detection with Closed Loop Control

Figure 9:
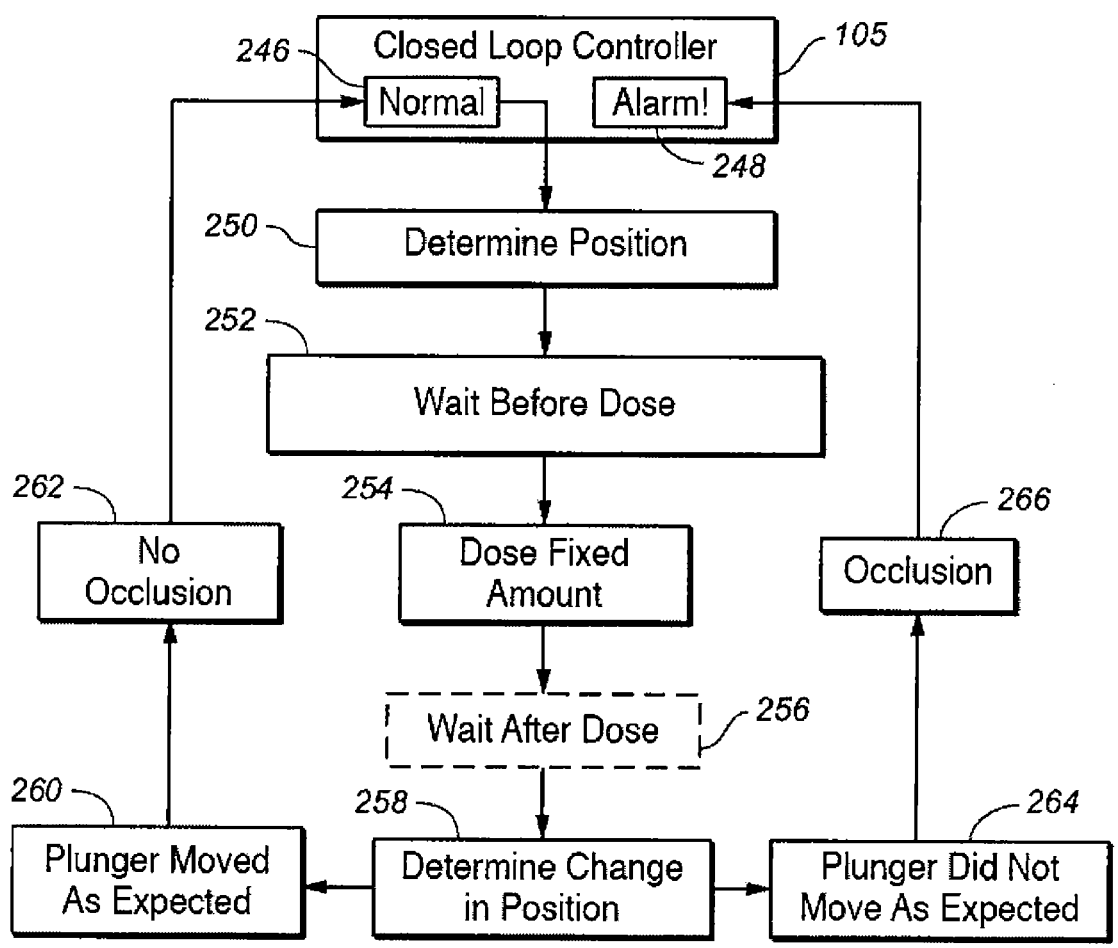
FIG. 9 is a flow diagram illustrating a method of detecting occlusions in an electrokinetic infusion pump with closed loop control according to an additional embodiment of the present invention.
Figure 10:
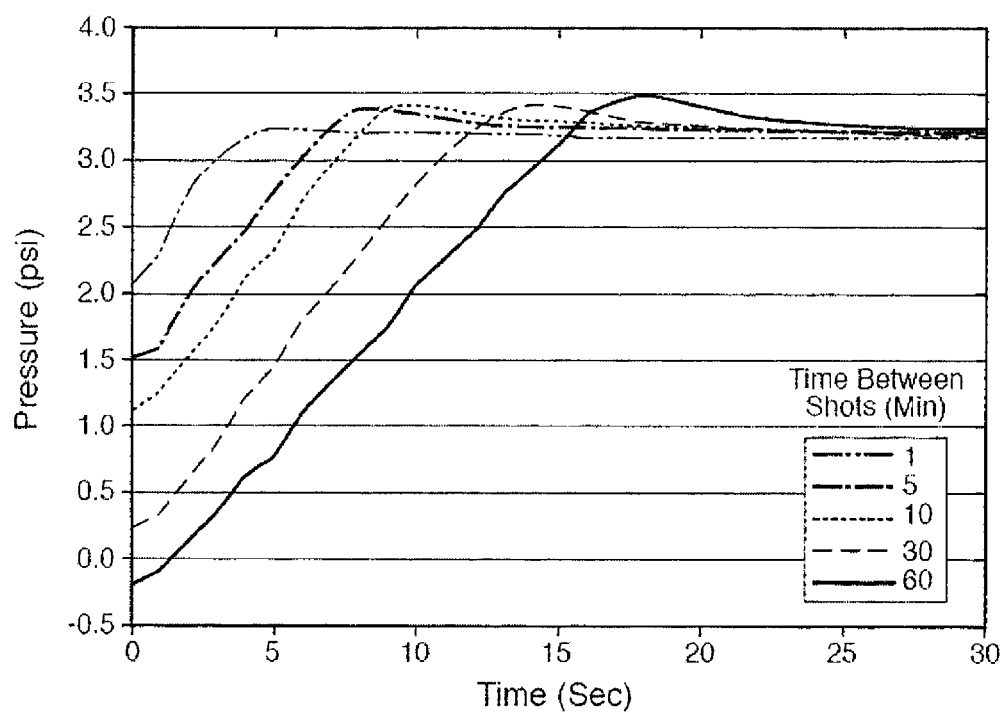
FIG. 10 is a graph illustrating back pressure in an electrokinetic infusion pump with closed loop control according to an embodiment of the present invention.
Figure 11:
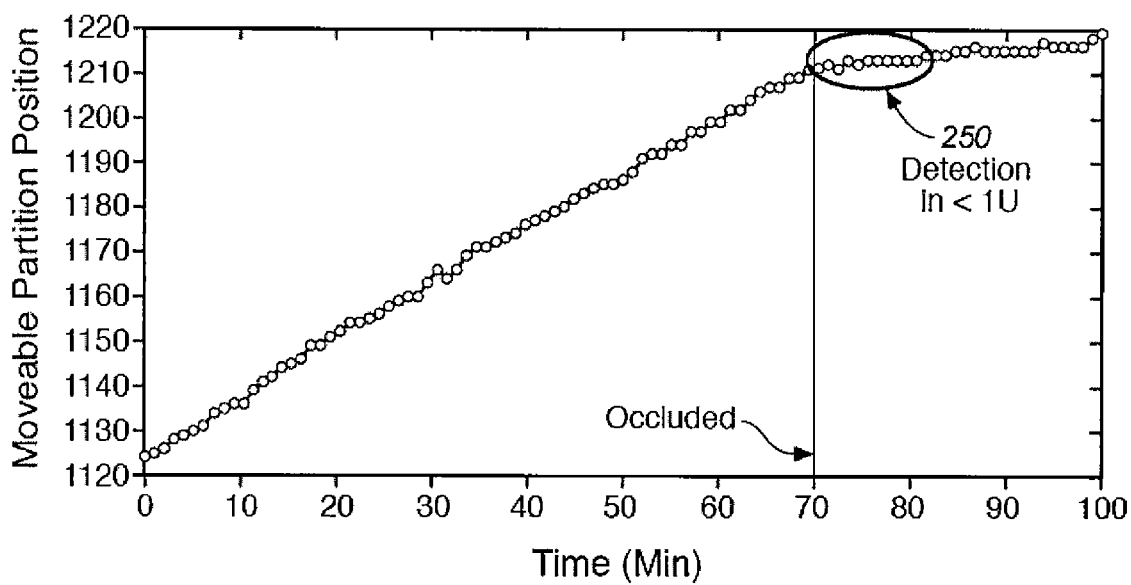
FIG. 11 is a graph illustrating the position of a moveable partition as a function of time when an occlusion occurs in an electrokinetic infusion pump with closed loop control according to an embodiment of the present invention.

FIG. 9 is a flow diagram illustrating a method of detecting occlusions in an electrokinetic infusion pump with closed loop control 100 according to an embodiment of the present invention. With reference to FIG. 9, and FIGS. 1 through 8, closed loop controller 105 starts with a normal status 246. In the next step, closed loop controller 105 determines position 250 of moveable partition 120. After determining the position 250 of moveable partition 120, closed loop controller 105 waits before dose 252. During this time, the pressure in electrokinetic infusion pump 103 decreases. After waiting before dose 252, a fixed volume is dosed 254. This is accomplished by activating the electrokinetic engine 102. As a result of dosing a fixed volume 254 (electrokinetic engine on time), the pressure in electrokinetic infusion pump 103 increases as a function of time, as illustrated in FIG. 10. Multiple graphs are illustrated in FIG. 10, showing the effect of time between shots (electrokinetic engine off time) on pressure in electrokinetic infusion pump 103. Waiting 1 minute between shots results in a rapid build up of pressure. Waiting 5 minutes between shots results in a longer time to build pressure. The rate at which pressure builds is the same in each graph, but the starting pressure decreases as a function of time between shots, and therefore results in longer times to build pressure. Each graph eventually reaches the same approximate pressure, in this case about 3.2 psi. This is the pressure needed to displace moveable partition 120. Returning to FIG. 9, after dosing a fixed amount 254, and waiting after dose 256 (during which time the pressure in electrokinetic infusion pump 103 increases), the change in position 258 of moveable partition 120 is determined. The position of moveable partition 120 can be determined using a variety of techniques, as mentioned previously. After determining the change in position 258 of moveable partition 120, closed loop controller 105 determines if moveable partition 120 has moved as expected 260, or if it has not moved as expected 264. If moveable partition 120 has moved as expected 260, then no occlusion 262 has occurred, and the closed loop controller 105 returns to normal status 246. If the moveable partition 120 has not moved as expected 264, then an occlusion 266 has occurred, and the closed loop controller 105 enters an alarm status 248. FIG. 11 is a graph illustrating the position of moveable partition 120 as a function of time when an occlusion occurs in an electrokinetic infusion pump with closed loop control 100, according to the embodiment described in the previous example (i.e., running with a series of on/off times using feedback control). As can be seen in FIG. 11, after about 70 minutes the rate at which moveable partition 120 moves as a function of time suddenly decreases in region 250. This indicates that an occlusion has occurred, blocking the movement of moveable partition 120.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for detecting a malfunction in an infusion pump having a non-mechanically driven movable partition, comprising:
    (a) for each of a plurality of instances:
        (i) activating the infusion pump for a first pre-determined amount of time to induce movement of the movable partition of the pump and to release a shot of fluid from the pump,
        (ii) de-activating the infusion pump for a second pre-determined amount of time, and
        (ii) determining a position of the movable partition using a sensor;
    (b) calculating a derivative for each of the plurality of instances, the derivative being based on a change in position of the movable partition with respect to a change in the number of shots released;
    (c) calculating a moving average using calculated derivative values corresponding to each of the plurality of instances; and
    (d) comparing the calculated moving average with a pre-determined threshold value, to determine whether the infusion pump is malfunctioning.

2. The method of claim 1, wherein the pre-determined threshold value is a minimum acceptable value for the calculated moving average.

3. The method of claim 2, wherein comparing the calculated moving average to the pre-determined threshold value further comprises triggering a positive occlusion flag if the calculated moving average is less than the pre-determined threshold value.

4. The method of claim 3, further comprising:
    serially repeating steps (i), (ii), (iii), (b), (c), and (d) during operation of the infusion pump,
    wherein the steps of comparing the calculated moving average include indicating the presence of an occlusion if the positive occlusion flag occurs at least a predetermined number of consecutive times.

5. The method of claim 4, wherein indicating the presence of an occlusion includes generating an alarm signal.

6. The method of claim 1, wherein the pre-determined threshold value is a maximum acceptable value for the calculated moving average.

7. The method of claim 6, wherein comparing the calculated moving average to the pre-determined threshold value further comprises triggering a positive fluid-loss condition flag if the calculated moving average is greater than the pre-determined threshold value.

8. The method of claim 7, further comprising:
    serially repeating steps (i), (ii), (iii), (b), (c), and (d) during operation of the infusion pump,
    wherein the steps of comparing the calculated moving average include indicating the presence of a fluid-loss condition if the positive fluid-loss condition flag occurs at least a predetermined number of consecutive times.

9. The method of claim 8, wherein indicating the presence of a fluid-loss condition includes generating an alarm signal.

10. The method of claim 1, wherein determining a position of the movable partition occurs before de-activating the infusion pump.

11. The method of claim 1, wherein calculating the derivative includes using a last two known positions of the moveable partition for each of the plurality of instances.

12. The method of claim 1, wherein the plurality of instances includes at least three instances.

13. The method of claim 1, wherein determining the position of the movable partition further comprises using a magnetic sensor.

14. The method of claim 1, wherein calculating the moving average includes multiplying the calculated derivative values by a weighting factor.

15. The method of claim 1, wherein the infusion pump is an electrokinetic infusion pump.

16. A system for detecting a malfunction in an infusion pump, comprising:
    an infusion pump having a non-mechanically driven movable partition disposed therein;
    a position sensor disposed on the pump;
    a controller associated with the infusion pump and adapted to operate the infusion pump in an activate/de-activate cycle, the cycle comprising activating the pump for a first pre-determined amount of time to induce movement of the movable partition and release a shot of fluid, and de-activating the pump for a second pre-determined amount of time; and
    a processor associated with the position sensor, the processor adapted to determine whether the infusion pump is malfunctioning at least by comparing a calculated moving average of a plurality of derivatives to a pre-determined threshold value, each derivative based on a change in position of the movable partition with respect to a change in the number of shots released by the pump.

17. The system of claim 16, wherein the position sensor comprises at least one of a magnetic sensor, an optical sensor, and a linear variable differential transformer.

18. The system of claim 16, wherein the pre-determined threshold value is a minimum acceptable value for the calculated moving average.

19. The system of claim 18, wherein the processor is configured to provide a positive occlusion flag if the calculated moving average is less than the pre-determined threshold value.

20. The system of claim 19, wherein the processor is configured to produce an occlusion detection signal if the positive occlusion flag signal is produced after each of at least a predetermined number of consecutive cycles.

21. The system of claim 20, wherein the predetermined number of cycles is at least three.

22. The system of claim 16, wherein the processor is configured to calculate the moving average based upon calculated derivatives from at least a last three cycles.

23. The system of claim 16, wherein the processor is configured to calculate the moving average based upon calculated derivatives from a last five cycles.

24. The system of claim 16, wherein the pre-determined threshold value is a maximum acceptable value for the calculated moving average.

25. The system of claim 24, wherein the processor is configured to provide a positive fluid-loss flag if the calculated moving average is greater than the pre-determined threshold value.

26. The system of claim 25, wherein the processor is adapted to produce a fluid-loss detection signal if the positive fluid-loss flag signal is produced after each of at least a predetermined number of consecutive cycles.

27. The system of claim 16, further comprising an alarm coupled to the processor for producing an alarm signal when the processor determines that the infusion pump is malfunctioning.

28. The system of claim 16, wherein the infusion pump is an electrokinetic infusion pump.

* * * * *